(12) United States Patent
Gagnon et al.

(10) Patent No.: US 10,105,331 B2
(45) Date of Patent: Oct. 23, 2018

(54) SUBSTITUTED AROMATIC COMPOUNDS AND PHARMACEUTICAL COMPOSITIONS FOR THE PREVENTION AND TREATMENT OF DIABETES

(71) Applicant: PROMETIC PHARMA SMT LIMITED, Comberton (GB)

(72) Inventors: Lyne Gagnon, Laval (CA); Brigitte Grouix, Montreal (CA)

(73) Assignee: PROMETIC PHARMA SMT LIMITED, Comberton, Cambridge (GB)

( * ) Notice: Subject to any disclaimer, the term of this patent is extended or adjusted under 35 U.S.C. 154(b) by 0 days.

(21) Appl. No.: 15/515,048

(22) PCT Filed: Oct. 8, 2015

(86) PCT No.: PCT/CA2015/000531
§ 371 (c)(1),
(2) Date: Mar. 28, 2017

(87) PCT Pub. No.: WO2016/054726
PCT Pub. Date: Apr. 14, 2016

(65) Prior Publication Data
US 2017/0209399 A1    Jul. 27, 2017

Related U.S. Application Data

(60) Provisional application No. 62/062,526, filed on Oct. 10, 2014.

(51) Int. Cl.
| | | |
|---|---|---|
| A61K 31/12 | (2006.01) |
| A61K 31/155 | (2006.01) |
| A61K 31/192 | (2006.01) |
| A61K 45/06 | (2006.01) |
| A61K 9/00 | (2006.01) |
| A61P 3/06 | (2006.01) |
| A61P 5/50 | (2006.01) |
| A61P 3/08 | (2006.01) |
| A61P 3/10 | (2006.01) |

(52) U.S. Cl.
CPC .......... *A61K 31/192* (2013.01); *A61K 9/0053* (2013.01); *A61K 31/155* (2013.01); *A61K 45/06* (2013.01); *A61P 3/06* (2018.01); *A61P 3/08* (2018.01); *A61P 3/10* (2018.01); *A61P 5/50* (2018.01); *A61K 31/12* (2013.01)

(58) Field of Classification Search
CPC ..... A61K 31/155; A61K 31/192; A61K 31/12
USPC ......................................... 514/675, 635, 866
See application file for complete search history.

(56) References Cited

FOREIGN PATENT DOCUMENTS

| WO | WO 2006/031931 A2 | 3/2006 | | |
|---|---|---|---|---|
| WO | WO 2012/097428 A1 | 7/2012 | | |
| WO | WO 2014/138906 A1 | 9/2014 | | |
| WO | WO-2016054726 A1 * | 4/2016 | ........... | A61K 31/155 |

* cited by examiner

*Primary Examiner* — Kevin E Weddington
(74) *Attorney, Agent, or Firm* — Saliwanchik, Lloyd & Eisenschenk

(57) ABSTRACT

The present invention concerns the use of compounds for preventing and/or treating diabetes, for modulating glucose, insulin, and/or triglyceride levels; for reducing blood glucose level; for maintaining or increasing insulin level; for increasing insulin secretion; increasing insulin sensitivity; or decreasing insulin resistance in a subject. These novel uses have been found for compounds represented by Formula I and pharmaceutically acceptable salts. wherein A is $C_5$ alkyl, $C_6$ alkyl, $C_5$ alkenyl, $C_6$ alkenyl, $C(O)$-$(CH_2)_n$—$CH_3$ or $CH(OH)$—$(CH_2)_n$—$CH_3$ wherein n is 3 or 4; $R_1$ is H, F or OH; $R_2$ is $C_5$ alkyl, $C_6$ alkyl, $C_5$ alkenyl, $C_6$ alkenyl, $C(O)$-$(CH_2)_n$—$CH_3$ or $CH(OH)$—$(CH_2)_n$—$CH_3$ wherein n is 3 or 4; $R_3$ is H, F, OH or $CH_2Ph$; $R_4$ is H, F or OH; Q is 1) $(CH_2)_mC(O)OH$ wherein m is 1 or 2, 2) $CH(CH_3)C(O)OH$, 3) $C(CH_3)_2C(O)OH$, 4) $CH(F)$—$C(O)OH$, 5) $CF_2$—$C(O)OH$, or 6) $C(O)$—$C(O)OH$.

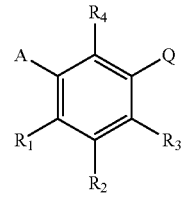

Formula I

30 Claims, 5 Drawing Sheets

SUBSTITUTED AROMATIC COMPOUNDS AND PHARMACEUTICAL COMPOSITIONS FOR THE PREVENTION AND TREATMENT OF DIABETES

CROSS REFERENCE TO A RELATED APPLICATION

This application is a National Stage Application of International Application Number PCT/CA2015/000531, filed Oct. 8, 2015; which claims priority to U.S. Provisional Application No. 62/062,526, filed Oct. 10, 2014; both of which are incorporated herein by reference in their entirety.

FIELD OF INVENTION

The present invention relates to the field of medicine. More particularly, the invention relates to methods, compositions and uses for prevention and/or treatment of diabetes and/or diabetes-related disorders.

BACKGROUND OF INVENTION

Diabetes is caused by multiple factors and is characterized by elevated levels of plasma glucose (hyperglycemia) in the fasting state. There are two generally recognized forms of diabetes: Type I diabetes, or insulin dependent diabetes, in which patients produce little or no insulin and Type II diabetes, or noninsulin-dependent diabetes wherein patients produce insulin, while at the same time demonstrating hyperglycemia. Type I diabetes is typically treated with exogenous insulin administered via injection. However, Type II diabetics often present "insulin resistance", such that the effect of insulin in stimulating glucose and lipid metabolism in the main insulin-sensitive tissues, namely muscle, liver and adipose tissues, is diminished and hyperglycemia results.

Persistent or uncontrolled hyperglycemia that occurs in diabetes is associated with increased morbidity and premature mortality. Abnormal glucose homeostasis is also associated, both directly and indirectly, with obesity, hypertension and alterations in lipid, lipoprotein and apolipoprotein metabolism. Type II diabetics are at increased risk of cardiovascular complications such as atherosclerosis, coronary heart disease, stroke, peripheral vascular disease, hypertension, nephropathy, retinopathy and also neuropathy. Many patients who have insulin resistance, but have not developed Type II diabetes, are also at risk of developing symptoms referred to as "Syndrome X", or "Metabolic Syndrome". Metabolic syndrome is characterized by insulin resistance, along with abdominal obesity, hyperinsulinemia, high blood pressure, low HDL (high density lipoproteins) and high VLDL (very low density lipoprotein), hypertriglyceridemia and hyperuricemia. Whether or not they develop overt diabetes, these patients are at increased risk of developing cardiovascular complications.

Current treatments for diabetes include: insulin, insulin secretagogues, such as sulphonylureas, which increase insulin production from pancreatic β-cells; glucose-lowering effectors, such as metformin which reduce glucose production from the liver; activators of the peroxisome proliferator-activated receptor-γ (PPAR-γ), such as the thiazolidinediones, which enhance insulin action; dipeptidyl peptidase-4 (DPP-4) inhibitors which inhibit the degradation of GLP-1 and α-glucuronidase inhibitors which interfere with gut glucose production. However, there are some deficiencies associated with these treatments. For example, sulphonylureas and insulin injections can be associated with hypoglycemia and weight gain. Responsiveness to sulphonylureas is often lost over time. An increased relative risk of pancreatic cancer and to a lesser extent other neoplasms has been linked to the use of DPP-4 inhibitors. Gastrointestinal problems are observed with metformin and α-glucosidase inhibitors. Finally, PPAR-γ agonists may cause increase weight and edema.

The present invention aims to address the needs for new treatment methods, compounds and pharmaceutical compositions for treating patients with diabetes and for treating patients with one or more disorders and conditions associated with abnormal levels of glucose, insulin, ketone bodies, plasma lipoprotein, triglycerides and the like.

International PCT publication WO 2014/138906 is a patent application filed previously by the present Applicant. That patent document describes compounds whose structure is related to the structure of the compounds of the present invention. However, that prior patent application is concerned with the treatment of fibrosis, not diabetes.

Additional features of the invention will be apparent from a review of the disclosure, figures and description of the invention herein.

BRIEF SUMMARY OF THE INVENTION

General aspects of the invention relates to the pharmaceutical use of compounds according to Formula I as defined herein, and pharmaceutically acceptable salts thereof.

Particular aspects of the invention relates to the use of compounds and compositions for the prevention and/or treatment of diabetes. Certain aspects concerns compounds according to Formula I as defined herein, and pharmaceutically acceptable salts thereof.

A particular aspect of the invention relates to a method for preventing and/or treating diabetes, said method comprising the step of administering to a subject in need thereof a compound represented by Formula I as defined herein, or a pharmaceutically acceptable salt thereof.

According to particular embodiments, the compounds and compositions of the invention relates to the prevention and/or treatment of Type I diabetes, Type II diabetes, Type III diabetes (Alzheimer), maturity-onset diabetes of the young, latent autoimmune diabetes of adults (LADA), gestational diabetes, hyperglycemia, glucose intolerance, insulin resistance, hyperinsulinemia, hypercholesterolemia, hyperlipoproteinemia, hyperlipidemia, hypertriglyceridemia, dyslipidemia, metabolic syndrome, syndrome X, diabetic neuropathy, diabetic retinopathy, atherosclerosis, sexual dysfunction, and metabolic syndrome. In one particular embodiment, the diabetes is Type II diabetes. In another particular embodiment, the diabetes is Type I diabetes.

Particular aspect of the invention relates to methods wherein administration of Formula I as defined herein, and/or pharmaceutically acceptable salts thereof, results in one or more of the following biological activities the subject: an increase in insulin secretion; an increase in insulin sensitivity; a decrease in insulin resistance; a decrease in blood glucose level; and a decrease of blood triglyceride level.

Another aspect of the invention relates to a method for modulating glucose, insulin and/or triglyceride levels in a subject in need thereof, comprising the step of administering to the subject a compound of Formula I, or a pharmaceutical acceptable salt thereof, as defined herein. In some embodiments, administration of the compound reduces blood glucose level. In some embodiments, the purpose of the method is for maintaining or increasing insulin level, and administration of the compound maintains or increases insulin level in a subject requiring protection and/or regeneration of pancreatic islets.

Another aspect of the invention relates to a method for increasing insulin secretion and/or increasing insulin sensitivity and/or decreasing insulin resistance in a subject in need thereof, comprising the step of administering to the subject a compound of Formula I, or a pharmaceutical acceptable salt thereof, as defined herein. In one embodiment the subject is afflicted by hyperglycemia, glucose intolerance, insulin resistance, hyperinsulinemia, dyslipidemia and/or loss of pancreatic function. In another embodiment, the compound is administered concomitantly with a second therapeutic agent (e.g. a compound for lowering or modulating blood glucose level such as metformin or is a thiazolidinedione).

Another aspect of the invention relates to a method for reducing blood triglyceride in a subject in need thereof, comprising the step of administering to the subject a compound of Formula I, or a pharmaceutical acceptable salt thereof, as defined herein, wherein the compound reduces blood triglyceride level. In one embodiment the subject is afflicted by diabetic dyslipidemia and/or metabolic syndrome.

Another aspect of the invention relates to the use of a compound of Formula I, or a pharmaceutical acceptable salt thereof, as defined herein, for the manufacture of a medicament for preventing and/or treating diabetes.

Another aspect of the invention relates to a compound of Formula I, or a pharmaceutical acceptable salt thereof, as defined herein, for use in the prevention or treatment of diabetes in a subject in need thereof.

Another aspect of the invention relates to a pharmaceutical composition comprising: (i) a compound of Formula I, or a pharmaceutical acceptable salt thereof, as defined herein; and (ii) a second therapeutic agent for lowering or modulating blood glucose level. In one embodiment the second therapeutic agent is metformin or thiazolidinedione. Preferably, the composition is adapted for an oral administration.

Further aspects of the invention will be apparent to a person skilled in the art from the following description, claims, and generalizations herein.

BRIEF DESCRIPTION OF THE FIGURES

FIG. 5A: C57BL/6 group (n=5); FIG. 5B: db/db Nx group (n=5); FIG. 5C: db/db Nx+ Compound I (10 mg/kg) group (n=5); FIG. 5D: db/db Nx+ Compound I (50 mg/kg) group (n=5).

DETAILED DESCRIPTION OF THE INVENTION

Figure 1:
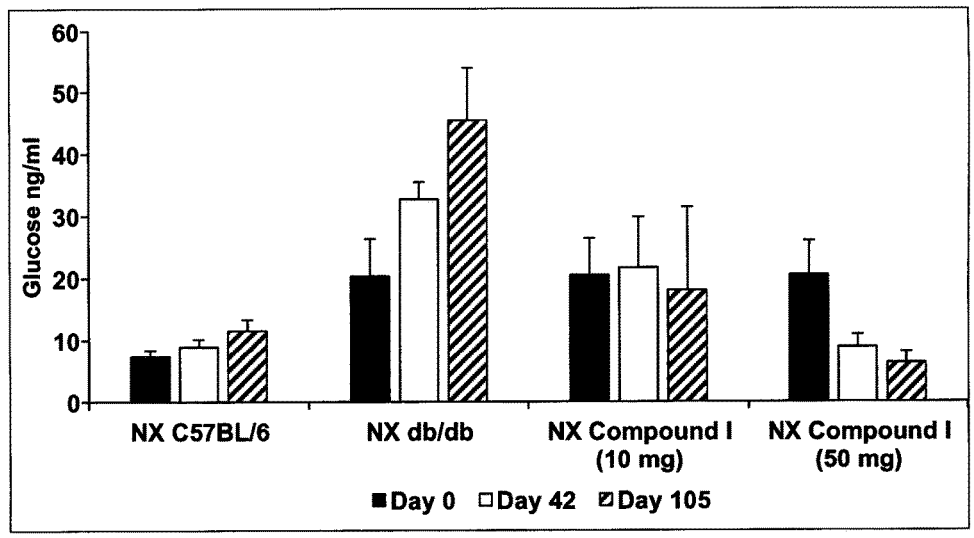
FIG. 1 is a bar graph showing that Compound I reduces blood glucose level down to normal level in uninephrectomized db/db mice, according to Example 3.

The present discloses compounds of Formula I, pharmaceutically acceptable salts thereof, compositions comprising same and uses thereof. Various embodiments of the present invention include:

A) Compounds of the Invention

According to one aspect, the invention concerns the pharmaceutical uses in the prevention and/or treatment of diabetes of compounds represented by Formula I, or pharmaceutically acceptable salts thereof:

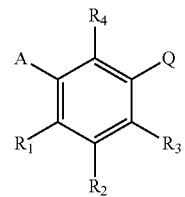

Formula I wherein

A is $C_5$ alkyl, $C_6$ alkyl, $C_5$ alkenyl, $C_6$ alkenyl, C(O)—$(CH_2)_n$—$CH_3$ or CH(OH)—$(CH_2)_n$—$CH_3$ wherein n is 3 or 4; or is preferably $C_5$ alkyl, $C_5$ alkenyl, C(O)—$(CH_2)_n$—$CH_3$ or CH(OH)—$(CH_2)_n$—$CH_3$ wherein n is 3; or is preferably $C_6$ alkyl, $C_6$ alkenyl, C(O)—$(CH_2)_n$—$CH_3$ or CH(OH)—$(CH_2)_n$—$CH_3$ wherein n is 4; or is preferably $C_5$ alkyl, $C_6$ alkyl, $C_5$ alkenyl, $C_6$ alkenyl; or $R_2$ is preferably $C_5$ alkyl or $C_5$ alkenyl; or $R_2$ is preferably $C_5$ alkyl or $C_6$ alkyl; or $R_2$ is preferably $C_5$ alkyl;

$R_1$ is H, F or OH;

$R_2$ is $C_5$ alkyl, $C_6$ alkyl, $C_5$ alkenyl, $C_6$ alkenyl, C(O)—$(CH_2)_n$—$CH_3$ or CH(OH)—$(CH_2)_n$—$CH_3$ wherein n is 3 or 4; or is preferably $C_5$ alkyl, $C_5$ alkenyl, C(O)—$(CH_2)_n$—$CH_3$ or CH(OH)—$(CH_2)_n$—$CH_3$ wherein n is 3; or is preferably $C_6$ alkyl, $C_6$ alkenyl, C(O)—$(CH_2)_n$—$CH_3$ or CH(OH)—$(CH_2)_n$—$CH_3$ wherein n is 4; or is preferably $C_5$ alkyl, $C_6$ alkyl, $C_5$ alkenyl, $C_6$ alkenyl; or is preferably straight chain $C_5$ alkyl, $C_6$ alkyl, $C_5$ alkenyl, $C_6$ alkenyl, C(O)—$(CH_2)_n$—$CH_3$ or CH(OH)—$(CH_2)_n$—$CH_3$ wherein n is 3 or 4; or $R_2$ is preferably $C_5$ alkyl or $C_5$ alkenyl; or $R_2$ is preferably $C_5$ alkyl or $C_6$ alkyl; or $R_2$ is preferably $C_5$ alkyl;

$R_3$ is H, F, OH or $CH_2Ph$; or is preferably H, OH or $CH_2Ph$;

$R_4$ is H, F or OH; or is preferably H;

Q is
1) $(CH_2)_mC(O)OH$ wherein m is 1 or 2, or m is preferably 1;
2) $CH(CH_3)C(O)OH$;
3) $C(CH_3)_2C(O)OH$;
4) $CH(F)$—$C(O)OH$;
5) $CF_2$—$C(O)OH$; or
6) $C(O)$—$C(O)OH$.

According to another aspect, the invention concerns the pharmaceutical uses in the prevention and/or treatment of diabetes of compounds represented by Formula I, or pharmaceutically acceptable salts thereof:

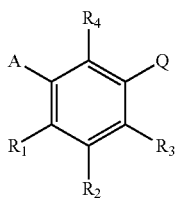

Formula I wherein
A is $C_5$ alkyl, $C_6$ alkyl, $C_5$ alkenyl, $C_6$ alkenyl, $C(O)$—$(CH_2)_n$—$CH_3$ or $CH(OH)$—$(CH_2)_n$—$CH_3$ wherein n is 3 or 4; or is preferably $C_5$ alkyl, $C_5$ alkenyl, $C(O)$—$(CH_2)_n$—$CH_3$ or $CH(OH)$—$(CH_2)_n$—$CH_3$ wherein n is 3; or is preferably $C_6$ alkyl, $C_6$ alkenyl, $C(O)$—$(CH_2)_n$—$CH_3$ or $CH(OH)$—$(CH_2)_n$—$CH_3$ wherein n is 4; or is preferably $C_5$ alkyl, $C_6$ alkyl, $C_5$ alkenyl, $C_6$ alkenyl; or $R_2$ is preferably $C_5$ alkyl or $C_5$ alkenyl; or $R_2$ is preferably $C_5$ alkyl or $C_6$ alkyl; or $R_2$ is preferably $C_5$ alkyl;

$R_1$ is H, F or OH;

$R_2$ is $C_5$ alkyl, $C_6$ alkyl, $C_5$ alkenyl, $C_6$ alkenyl, $C(O)$—$(CH_2)_n$—$CH_3$ or $CH(OH)$—$(CH_2)_n$—$CH_3$ wherein n is 3 or 4; or is preferably $C_5$ alkyl, $C_5$ alkenyl, $C(O)$—$(CH_2)_n$—$CH_3$ or $CH(OH)$—$(CH_2)_n$—$CH_3$ wherein n is 3; or is preferably $C_5$ alkyl, $C_6$ alkyl, $C(O)$—$(CH_2)_n$—$CH_3$ or $CH(OH)$—$(CH_2)_n$—$CH_3$ wherein n is 4; or is preferably $C_5$ alkyl, $C_6$ alkyl, $C_5$ alkenyl, $C_6$ alkenyl; or is preferably straight chain $C_5$ alkyl, $C_6$ alkyl, $C_5$ alkenyl, $C_6$ alkenyl, $C(O)$—$(CH_2)_n$—$CH_3$ or $CH(OH)$—$(CH_2)_n$—$CH_3$ wherein n is 3 or 4; or $R_2$ is preferably $C_5$ alkyl or $C_5$ alkenyl; or $R_2$ is preferably $C_5$ alkyl or $C_6$ alkyl; or $R_2$ is preferably $C_5$ alkyl;

$R_3$ is H, F, OH or $CH_2Ph$; or is preferably H, OH or $CH_2Ph$;

$R_4$ is H, F or OH; or is preferably H;

Q is
1) $(CH_2)_mC(O)OH$ wherein m is 1 or 2, or m is preferably 1;
2) $CH(F)$—$C(O)OH$;
3) $CF_2$—$C(O)OH$; or
4) $C(O)$—$C(O)OH$.

According to another aspect, the invention concerns the pharmaceutical uses in the prevention and/or treatment of diabetes of compounds represented by Formula I, or pharmaceutically acceptable salts thereof:

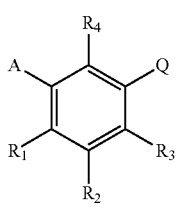

Forumla I wherein
A is $C_5$ alkyl, $C_6$ alkyl, $C_5$ alkenyl, $C_6$ alkenyl, $C(O)$—$(CH_2)_n$—$CH_3$ or $CH(OH)$—$(CH_2)_n$—$CH_3$ wherein n is 3 or 4; or is preferably $C_5$ alkyl, $C_5$ alkenyl, $C(O)$—$(CH_2)_n$—$CH_3$ or $CH(OH)$—$(CH_2)_n$—$CH_3$ wherein n is 3; or is preferably $C_6$ alkyl, $C_6$ alkenyl, $C(O)$—$(CH_2)_n$—$CH_3$ or $CH(OH)$—$(CH_2)_n$—$CH_3$ wherein n is 4; or is preferably $C_5$ alkyl, $C_6$ alkyl, $C_5$ alkenyl, $C_6$ alkenyl; or $R_2$ is preferably $C_5$ alkyl or $C_5$ alkenyl; or $R_2$ is preferably $C_5$ alkyl or $C_6$ alkyl; or $R_2$ is preferably $C_5$ alkyl;

$R_1$ is H or OH; or is preferably H;

$R_2$ is $C_5$ alkyl, $C_6$ alkyl, $C_5$ alkenyl, $C_6$ alkenyl, $C(O)$—$(CH_2)_n$—$CH_3$ or $CH(OH)$—$(CH_2)_n$—$CH_3$ wherein n is 3 or 4; or is preferably $C_5$ alkyl, $C_5$ alkenyl, $C(O)$—$(CH_2)_n$—$CH_3$ or $CH(OH)$—$(CH_2)_n$—$CH_3$ wherein n is 3; or is preferably $C_6$ alkyl, $C_6$ alkenyl, $C(O)$—$(CH_2)_n$—$CH_3$ or $CH(OH)$—$(CH_2)_n$—$CH_3$ wherein n is 4; or is preferably $C_5$ alkyl, $C_6$ alkyl, $C_5$ alkenyl, $C_6$ alkenyl; or is preferably straight chain $C_5$ alkyl, $C_6$ alkyl, $C_5$ alkenyl, $C_6$ alkenyl, $C(O)$—$(CH_2)_n$—$CH_3$ or $CH(OH)$—$(CH_2)_n$—$CH_3$ wherein n is 3 or 4; or $R_2$ is preferably $C_5$ alkyl or $C_5$ alkenyl; or $R_2$ is preferably $C_5$ alkyl or $C_6$ alkyl; or $R_2$ is preferably $C_5$ alkyl;

$R_3$ is H, OH or $CH_2Ph$; or is preferably H or OH;

$R_4$ is H or OH; or is preferably H;

Q is
1) $(CH_2)_mC(O)OH$ wherein m is 1;
2) $CH(F)$—$C(O)OH$;
3) $CF_2$—$C(O)OH$; or
4) $C(O)$—$C(O)OH$.

According to a particular embodiment, A is $C_5$ alkyl, $C_6$ alkyl, $C_5$ alkenyl, or $C_6$ alkenyl; or A is preferably $C_5$ alkyl or $C_5$ alkenyl; or A is preferably $C_5$ alkyl or $C_6$ alkyl; or A is preferably $C_5$ alkyl.

According to a particular embodiment, $R_1$ is H or OH, or $R_1$ is H.

According to a particular embodiment, $R_2$ is $C_5$ alkyl, $C_6$ alkyl, $C_5$ alkenyl, or $C_6$ alkenyl; or $R_2$ is $C_5$ alkyl or $C_5$ alkenyl; or $R_2$ is $C_5$ alkyl or $C_6$ alkyl; or $R_2$ is $C_5$ alkyl.

According to a particular embodiment, $R_3$ is H, OH or $CH_2Ph$, or $R_3$ is H or OH, or $R_3$ is H.

According to a particular embodiment, $R_4$ is H.

According to a particular embodiment, Q is $(CH_2)_mC(O)OH$, wherein m is 1 or 2.

According to a particular embodiment, Q is $(CH_2)_mC(O)OH$, wherein m is 1.

According to a particular embodiment, A is $C_5$ alkyl, $C_6$ alkyl, $C_5$ alkenyl, $C_6$ alkenyl; $R_1$ is H or OH; $R_2$ is $C_5$ alkyl, $C_6$ alkyl, $C_5$ alkenyl, $C_6$ alkenyl; $R_3$ is H, OH or $CH_2Ph$; $R_4$ is H; and Q is $(CH_2)_mC(O)OH$ wherein m is 1.

According to a particular embodiment, the compounds is the pharmaceutically acceptable salt of the compounds of Formula I.

As used herein, the term "alkyl" is intended to include both branched and straight chain saturated aliphatic hydrocarbon groups having the specified number of carbon atoms in a linear or branched arrangement, for example, $C_1$-$C_8$ as in $C_1$-$C_8$ alkyl is defined as including groups having 1, 2, 3, 4, 5, 6, 7 or 8 in a linear or branched arrangement. Examples of alkyl defined above include, but are not limited to, methyl, ethyl, n-propyl, i-propyl, n-butyl, t-butyl, i-butyl, pentyl, hexyl, heptyl and octyl. In preferred embodiments, the alkyl groups are linear alkyl groups.

As used herein, the term, "alkenyl" is intended to mean unsaturated straight or branched chain hydrocarbon groups having the specified number of carbon atoms therein, and in which at least two of the carbon atoms are bonded to each other by a double bond, and having either E or Z regio-chemistry and combinations thereof. For example, $C_2$-$C_6$ as in $C_2$-$C_6$ alkenyl is defined as including groups having 2, 3, 4, 5, or 6 carbons in a linear or branched arrangement, at least two of the carbon atoms being bonded together by a double bond. Examples of alkenyl include ethenyl (vinyl), 1-propenyl, 2-propenyl, and 1-butenyl. In preferred embodiments, the alkenyl groups are linear alkenyl groups.

Examples of compounds of Formula I include, but are not limited to, the compounds listed in Table 1 hereinafter. In a preferred embodiment, the compound is represented by the acid form or a pharmaceutically acceptable salt of any one of the following Compounds. In a particular embodiment, the compound is a pharmaceutically acceptable salt of any one of the following Compounds.

TABLE 1

Examples of compounds of Formula I

| Compound | Structure |
|---|---|
| I | |
| II | |
| III | |
| IV | |
| V | |
| VI | |
| VII | 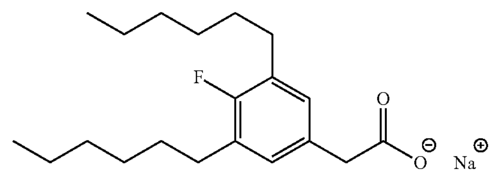 [SMILES: CCCCCCc1cc(CC(=O)[O-])cc(CCCCCC)c1F ; [Na+]] |
| VIII | 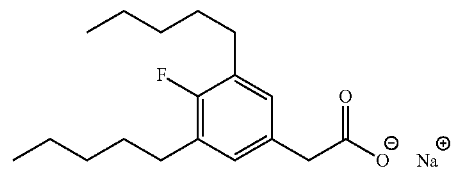 [SMILES: CCCCCc1cc(CC(=O)[O-])cc(CCCCC)c1F ; [Na+]] |
| IX | 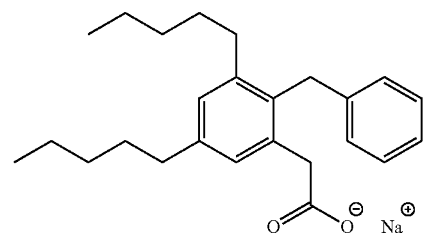 [SMILES: CCCCCc1cc(CCCCC)c(Cc2ccccc2)c(CC(=O)[O-])c1 ; [Na+]] |
| X | 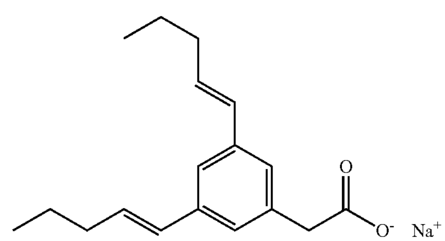 [SMILES: CCC/C=C/c1cc(/C=C/CCC)cc(CC(=O)[O-])c1 ; [Na+]] |
| XI | 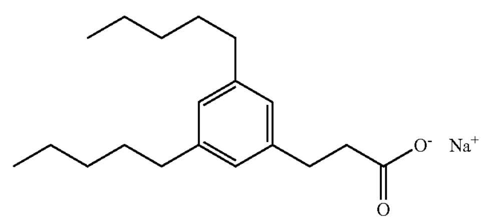 [SMILES: CCCCCc1cc(CCCCC)cc(CCC(=O)[O-])c1 ; [Na+]] |
| XII | 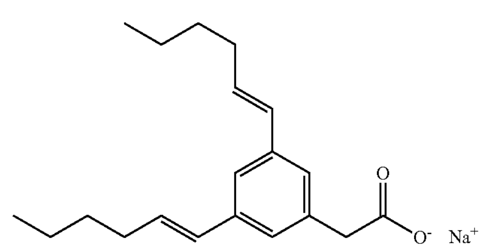 [SMILES: CCCC/C=C/c1cc(/C=C/CCCC)cc(CC(=O)[O-])c1 ; [Na+]] |
| XIII | 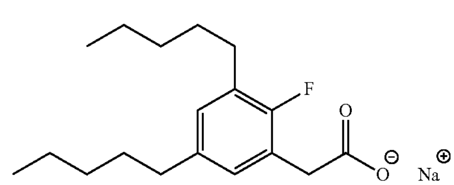 [SMILES: CCCCCc1cc(CCCCC)c(F)c(CC(=O)[O-])c1 ; [Na+]] |

TABLE 1-continued

Examples of compounds of Formula I

| Compound | Structure |
|---|---|
| XIV | 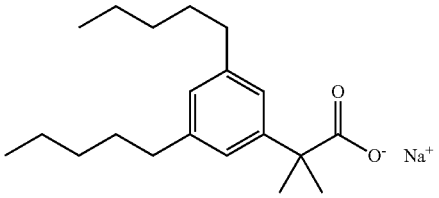 [SMILES: CCCCCc1cc(CCCCC)cc(C(C)(C)C(=O)[O-])c1 ; [Na+]] |

The Applicants have described elsewhere compounds whose structure is related to the structure of the compounds of the present invention. Reference is made for instance to the compounds disclosed in international PCT application No. PCT/CA2014/000236 filed on Mar. 14, 2014 (published as WO 2014/138906) entitled "Substituted Aromatic Compounds and Related Method for the Treatment of Fibrosis" which is incorporated herein by reference in its entirety. Accordingly, in particular embodiments any one or all the Compounds 1 to 8 disclosed in WO 2014/138906 are excluded from the scope of the present invention.

Salts

As used herein, the term "pharmaceutically acceptable salt" is intended to mean base addition salts. Example of pharmaceutically acceptable salts are also described, for example, in Berge et al., "Pharmaceutical Salts", *J. Pharm. Sci.* 66, 1-19 (1977). Pharmaceutically acceptable salts may be synthesized from the parent agent that contains an acidic moiety, by conventional chemical methods. Generally, such salts are prepared by reacting the free acid forms of these agents with a stoichiometric amount of the appropriate base in water or in an organic solvent, or in a mixture of the two. Salts may be prepared in situ, during the final isolation or purification of the agent or by separately reacting a purified compound of the invention in its free acid form with the desired corresponding base, and isolating the salt thus formed.

The pharmaceutically acceptable salt of the compounds of Formula I may be selected from the group consisting of base addition salts of sodium, potassium, calcium, magnesium, lithium, ammonium, manganese, zinc, iron, or copper. In preferred embodiments, the pharmaceutically acceptable salt of the compounds according to the invention may be the sodium, potassium, calcium, magnesium or lithium salt. More preferably the pharmaceutically acceptable salt is sodium.

In some embodiments, the compounds are the sodium salts listed in Table 1 hereinbefore. In a preferred embodiment, the compound is Compound I as defined herein.

All acid, salt and other ionic and non-ionic forms of the compounds described are included as compounds of the invention. For example, if a compound is shown as an acid herein, the salt forms of the compound are also included. Likewise, if a compound is shown as a salt and the acid forms are also included.

Prodrugs

In certain embodiments, the compounds of the present invention as represented by generalized Formula I wherein said compounds are present in the free carboxylic acid form, may also include all pharmaceutically acceptable salts, isosteric equivalents such as tetrazole and prodrug forms thereof. Examples of the latter include the pharmaceutically acceptable esters or amides obtained upon reaction of alcohols or amines, including amino acids, with the free acids defined by Formula I.

Chirality

The compounds of the present invention, their pharmaceutically acceptable salts, or prodrugs thereof, may contain one or more asymmetric centers, chiral axes and chiral planes and may thus give rise to enantiomers, diastereomers, and other stereoisomeric forms and may be defined in terms of absolute stereochemistry, such as (R)- or (S)-. The present invention is intended to include all such possible isomers, as well as, their racemic and optically pure forms. Optically active (+) and (−), (R)- and (S)-isomers may be prepared using chiral synthons or chiral reagents, or resolved using conventional techniques, such as reverse phase HPLC. The racemic mixtures may be prepared and thereafter separated into individual optical isomers or these optical isomers may be prepared by chiral synthesis. The enantiomers may be resolved by methods known to those skilled in the art, for example by formation of diastereoisomeric salts which may then be separated by crystallization, gas-liquid or liquid chromatography, selective reaction of one enantiomer with an enantiomer specific reagent. It will also be appreciated by those skilled in the art that where the desired enantiomer is converted into another chemical entity by a separation technique, an additional step is then required to form the desired enantiomeric form. Alternatively specific enantiomers may be synthesized by asymmetric synthesis using optically active reagents, substrates, catalysts, or solvents or by converting one enantiomer to another by asymmetric transformation.

Certain compounds of the present invention may exist in Zwitterionic form and the present invention includes Zwitterionic forms of these compounds and mixtures thereof.

Hydrates

In addition, the compounds of the invention also may exist in hydrated and anhydrous forms. Hydrates of any of the formulas described herein are included as compounds of the invention which may exist as a monohydrate or in the form of a polyhydrate.

B) Methods of Preparation

In general, all compounds of the present invention may be prepared by any conventional methods, using readily available and/or conventionally preparable starting materials, reagents and conventional synthesis procedures. Of particular interest is the work of Hundertmark, T.; Littke, A. F.; Buchwald, S. L.; Fu, G. C. *Org. Lett.* 2000, 12, pp. 1729-1731.

The exemplification section hereinafter provides general schemes and specific, but non limitative, examples for the synthesis of Formula I. Those skilled in the art may also refer to the Applicants published PCT application WO 2014/138906 (incorporated herein by reference in its entirety) disclosing compounds whose structure is related to the structure of some of the compounds of the present invention.

C) Pharmaceutical Applications

As indicated and exemplified herein, the compounds of the present invention have beneficial pharmaceutical properties and these compounds may have useful pharmaceutical applications in the prevention and/or treatment of various diseases and/or conditions in a subject. Medical and pharmaceutical applications contemplated by the inventors include, but are not limited to, those diseases and conditions where abnormal blood levels of glucose, abnormal blood levels of insulin, abnormal levels of ketone bodies in the urine, abnormal levels of plasma lipoprotein and/or abnormal blood levels of triglycerides are an issue. In particular embodiments, the medical and pharmaceutical applications contemplated by the inventors concerns diabetes.

The term "subject" includes living organisms in which abnormal blood levels of glucose, abnormal blood levels of insulin, abnormal levels of ketone bodies in the urine, abnormal levels of plasma lipoprotein and/or abnormal blood levels of triglycerides can occur, or which are susceptible to such conditions. The term "subject" includes animals such as mammals or birds. Preferably, the subject is a mammal, including but not limited to a human, a horse, a dog and a cat. In some embodiments, mice are excluded from the scope of a mammal. More preferably, the subject is a human. Most preferably, the subject is a human patient in need of treatment, including but not limited to a diabetic patient.

As used herein, "preventing" or "prevention" is intended to refer to at least the reduction of likelihood of the risk of (or susceptibility to) acquiring a disease or disorder (i.e., causing at least one of the clinical symptoms of the disease not to develop in a patient that may be exposed to or predisposed to the disease but does not yet experience or display symptoms of the disease). Biological and physiological parameters for identifying such patients are provided herein and are also well known by physicians. In preferred embodiments, "preventing" or "prevention" refers to preventing decrease in insulin secretion or insulin resistance, and/or to reducing risk of diabetes or loss of pancreatic function.

The terms "treatment of" or "treating a subject" includes the application or administration of a compound of the invention to a subject (or application or administration of a compound of the invention to a cell or tissue from a subject) with the purpose of delaying, stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indication of success in the treatment or amelioration of an injury, pathology or condition, including any objective or subjective parameter such as abatement; remission; lessening of the rate of worsening; lessening severity of the disease; stabilization, diminishing of symptoms or making the injury, pathology or condition more tolerable to the subject; slowing in the rate of degeneration or decline; making the final point of degeneration less debilitating; or improving a subject's physical or mental well-being. In some embodiments, the term "treating" can include increasing a subject's life expectancy and/or delay before additional treatments are required (e.g., surgery, dialysis or transplantation). In preferred embodiments, "treatment" or "treating" refers to improving the medical condition of subjects afflicted by insulin resistance, hyperinsulinemia, hyperglycemia and/or hyperlipidemia.

Diabetes

Addressing "diabetes" and "glucose-lipid-related metabolic disorder" is among the medical and pharmaceutical applications contemplated by the present invention. Diabetes mellitus, often simply referred to as diabetes, is characterized by a group of metabolic diseases in which a person has high blood sugar, either because the body does not produce enough insulin, or because cells do not respond to the insulin that is produced. As used herein, the term "diabetes" broadly encompasses different types or forms of diabetes and also encompass metabolic-related conditions or disorders including, but not limited to, Type I diabetes, Type II diabetes, maturity-onset diabetes of the young, latent autoimmune diabetes of adults (LADA), gestational diabetes, obesity, hyperglycemia, glucose intolerance, insulin resistance, hyperinsulinemia, hypercholesterolemia, hyperlipoproteinemia, hyperlipidemia, hypertriglyceridemia, dyslipidemia, metabolic syndrome, syndrome X, diabetic neuropathy, diabetic retinopathy, atherosclerosis sexual dysfunction, metabolic syndrome. In preferred embodiments, the present invention relates to methods, compounds and compositions where high blood sugar is a medical problem, e.g. Type I and Type II diabetes. In preferred embodiments, the present invention relates to methods, compounds and compositions where insulin resistance is a medical problem, e.g. Type I and Type II diabetes.

As is known, various diseases and conditions may cause diabetes, and the present invention may be useful in preventing and/or treating, directly or indirectly, one or more of these causes: drug-induced diabetes such as but not limited to streptozotocin, alloxan, rodenticide Vacor, theophylline, aspirin, nalidixic acid, thiazide, antihypentensive vasodilator diazoxide, corticosteroids, beta-blockers, low estrogen, autoimmune thyroid disease, thyrotoxicosis, pesticide-induced diabetes. Also many diseases may be a direct cause arising from diabetes or insulin insensivity or insulin resistance such as Alzheimer (type 3 diabetes).

Without being bound by any theory, the compounds of the invention may increase the regeneration or prevent the apoptosis of islets of Langerhans to prevent or ameliorate the symptoms of diabetes mellitus. The compounds and compositions of the invention may also: (1) restore beta-cell mass and function in an individual in need thereof; (2) prevent or treat type I diabetes in an individual in need thereof; (3) prevent or treat type II diabetes in an individual in need thereof; (4) prevent or treat latent autoimmune diabetes of adults (LADA) in an individual in need thereof; (5) treat type II diabetes by preserving or increasing the number of functional insulin-producing cells (e.g., beta-cells) and/or (6) decrease resistance to insulin and/or increasing insulin sensitivity. The present invention encompasses these and other possible mechanisms of action.

A related aspect of the invention concerns methods for positively affecting in a human subject in need thereof at least one pancreatic function parameter, such as: (i) size, growth and/or secreting activity of islets of Langerhans; (ii) size, growth and/or secreting activity of beta-cells; (iii) insulin secretion; (iv) insulin blood levels and (v) glucose blood levels. The method comprises administering to said human subject a compound represented by any of Formula I described herein or a pharmaceutically acceptable salt, whereby the administration positively affects in the human subject at least one of said pancreatic function parameter.

Preferably, the administration of one or more compounds according to the invention provides in the human subject at least one of the following benefits: (1) restoration of beta-cell mass and/or function; (2) prevention and/or treatment of type I and type II diabetes; (3) prevention and/or treatment of latent autoimmune diabetes; (4) preservation and/or increase in the number of functional insulin-producing cells; and/or (5) decrease of resistance to insulin and/or increase to insulin sensitivity.

Accordingly, related aspects of the invention concerns the use of compounds as defined herein for modulating glucose, insulin and/or lipid levels in a subject, and more particularly in subjects suffering from obesity; hypoglycemia, hyperglycemia, and/or glucose intolerance; insulin resistance and/or hyperinsulinemia; and dyslipidemia (e.g., hyperlipidemia, hypercholesterolemia, hyperlipoproteinemia, and/or hypertriglyceridemia).

Other Diseases

As indicated hereinbefore, chronic hyperglycemia that is characteristic of diabetes and is associated, both directly and indirectly, with a number of other diseases and unhealthy outcomes linked to increased risk of disease. Examples of such diseases include metabolic syndrome, syndrome X, dyslipidemia, hyperlipidemia, hyperlipoproteinemia, diabetic retinopathy, atherosclerosis, and sexual dysfunction. Therefore, a compound that can lower significantly blood sugar concentration, such as the compounds described herein and exemplified in the present invention, may conceivably provide therapeutic benefits for diseases associated with diabetes.

Pharmaceutical Compositions and Formulations

As indicated hereinbefore, the compounds of the invention have many potential therapeutic applications. Therefore, a related aspect of the invention concerns pharmaceutical compositions comprising a therapeutically effective amount of one or more of the compounds of the invention described herein and a pharmaceutically acceptable carrier, diluent or excipient.

As used herein, the term "pharmaceutical composition" refers to the presence of at least one compound of the invention according to Formula I as defined herein and at least one pharmaceutically acceptable carrier, diluent, vehicle or excipient.

As used herein, the term "pharmaceutically acceptable carrier", "pharmaceutically acceptable diluent or "pharmaceutically acceptable excipient" is intended to mean, without limitation, any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, emulsifier, or encapsulating agent, such as a liposome, cyclodextrins, encapsulating polymeric delivery systems or polyethyleneglycol matrix, which is acceptable for use in subjects, preferably humans. It preferably refers to a compound or composition that is approved or approvable by a regulatory agency of the Federal or State government or listed in the U.S. Pharmacopoeia or other generally recognized pharmacopoeia for use in animals and more particularly in humans. The pharmaceutically acceptable vehicle can be a solvent or dispersion medium containing, for example, water, ethanol, polyol (for example, glycerol, propylene glycol, and liquid polyethylene glycol), suitable mixtures thereof, and vegetable oils. Additional examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate. Prevention of the action of microorganisms can be achieved by addition of antibacterial and antifungal agents, for example, parabens, chlorobutanol, phenol, ascorbic acid, thimerosal, and the like. In many cases, isotonic agents are included, for example, sugars, sodium chloride, or polyalcohols such as mannitol and sorbitol, in the composition. Prolonged absorption of injectable compositions can be brought about by including in the composition an agent which delays absorption, for example, aluminum monostearate or gelatin.

As used herein, the term "therapeutically effective amount" means the amount of compound that, when administered to a subject for treating or preventing a particular disorder, disease or condition, is sufficient to effect such treatment or prevention of that disorder, disease or condition. Dosages and therapeutically effective amounts may vary for example, depending upon a variety of factors including the activity of the specific agent employed, the age, body weight, general health, gender, and diet of the subject, the time of administration, the route of administration, the rate of excretion, and any drug combination, if applicable, the effect which the practitioner desires the compound to have upon the subject and the properties of the compounds (e.g., hydrophobicity, solubility, bioavailability, stability, potency, toxicity, etc.), and the particular disorder(s) the subject is suffering from. In addition, the therapeutically effective amount may depend on the subject's blood parameters (e.g., lipid profile, insulin levels, glycemia), the severity of the disease state, organ function, or underlying disease or complications. Such appropriate doses may be determined using any available assays including the assays described herein. When one or more of the compounds of the invention is to be administered to humans, a physician may for example, prescribe a relatively low dose at first, subsequently increasing the dose until an appropriate response is obtained. In general, however, it is envisioned that the dose for the present compounds may be in the range of about 0.01 to about 50 mg/kg per day. In selected embodiments, the range may be between 0.01 to 20 mg/kg per day. In selected embodiments, the range may be between 0.01 to 10 mg/kg per day. In selected embodiments, the range may be between 0.1 to 10 mg/kg per day. In selected embodiments, the range may be between 0.1 to 5 mg/kg per day. In selected embodiments, the range may be between 1 to 10 mg/kg per day.

In some embodiments, the compositions of the invention comprise a therapeutically effective amount of a compound of Formula I. An example of a preferred compound is Compound I. As indicated hereinbefore, the compositions concern pharmaceutical compositions comprising one or more of the compounds of the invention described herein (e.g., a compound of Formula I). As indicated hereinbefore, the pharmaceutical compositions of the invention may be particularly useful for subjects afflicted by, or likely to be affected by, diabetes.

In some embodiments, the invention pertains to pharmaceutical compositions that include a therapeutically effective amount of one or more compounds of Formula I for increasing insulin secretion and/or increasing insulin sensitivity in a subject in need thereof.

In some embodiments, the invention pertains to pharmaceutical compositions that include a therapeutically effective amount of one or more compounds of Formula I for decreasing insulin resistance in a subject in need thereof.

In some embodiments, the invention pertains to pharmaceutical compositions that include a therapeutically effective amount of one or more compounds of Formula I for decreasing hyperglycemia in a subject in need thereof.

In some embodiments, the invention pertains to pharmaceutical compositions that include a therapeutically effective amount of one or more compounds of Formula I for reducing blood triglyceride in a subject.

The compounds of the invention may be formulated prior to administration into pharmaceutical compositions using available techniques and procedures. For instance, the pharmaceutical compositions may be formulated in a manner suitable for administration by oral, intravenous (iv), intramuscular (im), depo-im, subcutaneous (sc), depo-sc, sublingually, intranasal, intrathecal, topical or rectal routes.

Preferably, the compound(s) of the invention can be orally administered. The formulations may conveniently be presented in unit dosage form and may be prepared by any methods well known in the art of pharmacy. Methods of preparing these formulations or compositions include the step of bringing into association a compound of the present invention with a pharmaceutically acceptable vehicle (e.g., an inert diluent or an assimilable edible carrier) and, optionally, one or more accessory ingredients. In general, the formulations are prepared by uniformly and intimately bringing into association a compound of the present invention with liquid carriers, or finely divided solid carriers, or both, and then, if necessary, shaping the product. The amount of the therapeutic agent in such therapeutically useful compositions is such that a suitable dosage will be obtained.

Formulations of the invention suitable for oral administration may be in the form of capsules (e.g., hard or soft shell gelatin capsule), cachets, pills, tablets, lozenges, powders, granules, pellets, dragees, e.g., coated (e.g., enteric coated) or uncoated, or as a solution or a suspension in an aqueous or non-aqueous liquid, or as an oil-in-water or water-in-oil liquid emulsion, or as an elixir or syrup, or as pastilles or as mouth washes and the like, each containing a predetermined amount of a compound of the present invention as an active ingredient. A compound of the present invention may also be administered as a bolus, electuary or paste, or incorporated directly into the subject's diet. Moreover, in certain embodiments these pellets can be formulated to: (a) provide for instant or rapid drug release (i.e., have no coating on them); (b) be coated, e.g., to provide for sustained drug release over time; or (c) be coated with an enteric coating for better gastrointestinal tolerability. Coating may be achieved by conventional methods, typically with pH or time-dependent coatings, such that the compound(s) of the invention is released in the vicinity of the desired location, or at various times to extend the desired action. Such dosage forms typically include, but are not limited to, one or more of cellulose acetate phthalate, polyvinylacetate phthalate, hydroxypropyl methyl cellulose phthalate, ethyl cellulose, waxes, and shellac. In solid dosage forms for oral administration a compound of the present invention may be mixed with one or more pharmaceutically acceptable carriers known in the art.

Peroral compositions typically include liquid solutions, emulsions, suspensions, and the like. The pharmaceutically acceptable vehicles suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, tragacanth, and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Pharmaceutical compositions suitable for injectable use may include sterile aqueous solutions (where water soluble) or dispersions and sterile powders for the extemporaneous preparation of sterile injectable solutions or dispersions. In all cases, the composition must be sterile and must be fluid to the extent that easy syringability exists. It must be stable under the conditions of manufacture and storage and must be preserved against the contaminating action of microorganisms such as bacteria and fungi. Sterile injectable solutions can be prepared by incorporating the therapeutic agent in the required amount in an appropriate solvent with one or a combination of ingredients enumerated above, as required, followed by filtered sterilization. Generally, dispersions are prepared by incorporating the therapeutic agent into a sterile vehicle which contains a basic dispersion medium and the required other ingredients from those enumerated above. In the case of sterile powders for the preparation of sterile injectable solutions, the methods of preparation are vacuum drying and freeze-drying which yields a powder of the active ingredient (i.e., the therapeutic agent) plus any additional desired ingredient from a previously sterile-filtered solution thereof.

Some pharmaceutical formulations may be suitable for administration as an aerosol, by inhalation. These formulations comprise a solution or suspension of the desired compound of Formula I as defined herein or a plurality of solid particles of such compound(s). For instance, metal salts of the compounds of this invention are expected to have physical chemical properties amenable with the preparation of fine particles of active pharmaceutical ingredient (API) for administration by inhalation but not the free acid form of these compounds. The desired formulation may be placed in a small chamber and nebulized. Nebulization may be accomplished by compressed air or by ultrasonic energy to form a plurality of liquid droplets or solid particles comprising the agents or salts. The liquid droplets or solid particles should have a particle size in the range of about 0.5 to about 5 microns. The solid particles can be obtained by processing the solid agent of any compound of Formula I described herein, or a salt thereof, in any appropriate manner known in the art, such as by micronization. The size of the solid particles or droplets will be, for example, from about 1 to about 2 microns. In this respect, commercial nebulizers are available to achieve this purpose. A pharmaceutical formulation suitable for administration as an aerosol may be in the form of a liquid, the formulation will comprise a water-soluble agent of any Formula described herein, or a salt thereof, in a carrier which comprises water. A surfactant may be present which lowers the surface tension of the formulation sufficiently to result in the formation of droplets within the desired size range when subjected to nebulization.

The compositions of this invention may also be administered topically to a subject, e.g., by the direct laying on or spreading of the composition on the epidermal or epithelial tissue of the subject, or transdermally via a "patch". Such compositions include, for example, lotions, creams, solutions, gels and solids. These topical compositions may comprise an effective amount, usually at least about 0.1%, or even from about 1% to about 5%, of a compound of the invention. Suitable carriers for topical administration typically remain in place on the skin as a continuous film, and resist being removed by perspiration or immersion in water. Generally, the carrier is organic in nature and capable of having dispersed or dissolved therein the therapeutic agent. The carrier may include pharmaceutically acceptable emollients, emulsifiers, thickening agents, solvents and the like.

Other compositions useful for attaining systemic delivery of the subject agents may include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

The compound(s) of the invention may also be administered parenterally or intraperitoneally. For such compositions, the compound(s) of the invention can be prepared in glycerol, liquid polyethylene glycols, and mixtures thereof and in oils. Under ordinary conditions of storage and use, these preparations may contain a preservative to prevent the growth of microorganisms.

Co-Administration

While it is within the scope of the invention to use the compounds defined herein as a monotherapy, these compounds can be used in combination with other techniques (e.g., diet) and/or in combination with existing agents (e.g., antidiabetic drugs).

Accordingly, the method and compositions of the present invention may also include co-administration of at least one compound of Formula I as defined herein, together with the administration of another therapeutically effective agent for the prevention and/or treatment of disorders and conditions associated with abnormal levels of glucose, insulin, ketone bodies, plasma lipoprotein and/or triglycerides.

Examples of anti-diabetic agents which may be used in combination with the compounds of the present invention include insulin (injection, inhaled, short-acting, long-acting, intermediate-acting, rapid-acting, premixed), insulin secretagogues (sulfonylurea, meglitinides), alpha-glucosidase inhibitors, incretin agent, TZDs, DDP-4 inhibitors and anti-obesity agents.

In one embodiment, the compound(s) of the invention is used in combination with at least one second therapeutic agent for lowering or controlling blood glucose level, that second therapeutic agent being a known compound which is currently being used or which is in development for preventing and/or treating diabetes. Examples of such known compounds include but are not limited to common anti-diabetic drugs such as sulphonylureas (e.g., glicazide, glipizide), metformin, glitazones (e.g., rosiglitazone, pioglitazone), prandial glucose releasing agents (e.g., repaglinide, nateglinide) and acarbose. A more detailed but non-limitative list of useful antidiabetic compounds or agents that can be used in combination with the compound(s) of the invention include insulin, biguanides, such as, for example metformin (Glucophage®, Bristol-Myers Squibb Company, U.S.; Stagid®, Lipha Sante, Europe); sulfonylurea drugs, such as, for example, gliclazide (Diamicron®), glibenclamide, gilpizide (Glucotrot® and Glucotrol XL®, Pfizer), glimepiride (Amaryl®, Aventis), chlorpropamide (e.g., Diabinese®, Pfizer), tolbutamide, and glyburide (e.g., Micronase®, Glynase®, and Diabeta®); glinides, such as, for example, repaglinide (Prandin® or NovoNorm®; Novo Nordisk), ormitiglinide, nateglinide (Starlix®), senaglinide, and BTS-67582; DPP-4-inhibitors such as vildagliptin and sitagliptin; insulin sensitizing agents, such as, for example, glitazones, a thiazolidinedione such as rosiglitazone maleate (Avandia®, Glaxo SmithKline), pioglitazone (Actos®, Eli Lilly, Takeda), troglitazone, ciglitazone, isaglitazone, darglitazone, englitazone; glucagon-like peptide I (GLP-1) receptor agonists, such as, for example, Exendin-4 (1-39) (Ex-4), Byetta™ (Amylin Pharmaceuticals Inc.), CJC-1 131 (Conjuchem Inc.), NN-221 I(Scios Inc.), GLP-1 agonists as those described in WO 98/08871; agents that slow down carbohydrate absorption, such as, for example, α-glucosidase inhibitors (e.g., acarbose, miglitol, voglibose, and emiglltate); agents that inhibit gastric emptying, such as, for example, glucagon-like peptide 1, cholescystokinin, amylin, and pramlintide; glucagon antagonists, such as, for example, quinoxaline derivatives (e.g., 2-styryl-3-[3-(dimethylamino) propylmethylaminol-6, 7-dichloroquinoxaline, Collins et al., Bioorganic and Medicinal Chemistiy Letters 2(9):91 5-91 8, 1992), skyrin and skyrin analogs (e.g., those described in WO 94/14426), 1-phenyl pyrazole derivatives (e.g., those described in U.S. Pat. No. 4,359,474), substituted disllacyclohexanes (e.g., those described in U.S. Pat. No. 4,374,130), substituted pyridines and biphenyls (e.g., those described in WO 98/04528), substituted pyridyl pyrroles (e.g., those described in U.S. Pat. No. 5,776,954), 2,4-diaryl-5-pyridylimidazoles (e.g., those described in WO 98/21957, WO 98/22108, WO 98/22109, and U.S. Pat. No. 5,880,139), 2,5-substituted aryl pyrroles (e.g., those described in WO 97/1 6442 and U.S. Pat. No. 5,837,719), substituted pyrimidinone, pyridone, and pyrimidine compounds (e.g., those described in WO 98/24780, WO 98/24782, WO 99/24404, and WO 99/32448), 2-(benzirnidazol-2-ylthio)-1-(3,4-dihydroxyphenyl)-1-ethanones (see Madsen et al., J. Med. Chem. 41:5151-5157, 1998), alkylidene hydrazides (e.g., those described in WO 99/01423 and WO 00/39088), glucokinase activators, such as, for example, those described in WO 00/58293, WO 01/44216, WO 01/83465, WO 01/83478, WO 01/85706, and WO 01/85707 and other compounds, such as selective ADP-sensitive $K^+$ channels activators (e.g., diazoxide), hormones (e.g., cholecytokinin, GRP-bombesin, and gastrin plus EGF receptor ligands; see Banerjee et al. Rev Diabet Stud, 2005 2(3): 165-176); peroxisome proliferator-activated receptor-gamma (PPAR-gamma) agonist (e.g., pioglitazone; see Ishida et al., Metabolism, 2004, 53(4), 488-94); antioxidants (e.g., 1-bis-o-hydroxycinnamoylmethane, curcuminoid bis-demethoxycurcumin; see Srivivasan et al., J Pharm Pharm Sci. 2003, 6(3): 327-33), WO 00/69810, WO 02/00612, WO 02/40444, WO 02/40445, WO 02140446, and the compounds described in WO 97/41097 (DRF-2344), WO 97/41119, WO 97/41120, WO 98/45292, WO 99/19313 (NN622/DRF-2725), WO 00/23415, WO 00/23416, WO 00/23417, WO 00/23425, WO 00/23445, WO 00/23451, WO 00/41121, WO 00/50414, WO 00/63153, WO 00/63189, WO 00/63190, WO 00/63191, WO 00/63192, WO 00/63193, WO 00/63196, WO 00/63209, U.S. Pat. No. 6,967,019, U.S. Pat. No. 7,101,845, U.S. Pat. No. 7,074,433, U.S. Pat. No. 6,992,060, U.S. Pat. No. RE39,062, WO 2006/131836; WO 2006/120574, WO 2004/1076276, WO 2004/041266, WO 2005/086661; EP 1 630 152, EP 1 559 422, U.S. No. 2004/0038126, US No. 2006/004012, WO 2010/127440 U.S. No. 2007/0066647; and the compounds referred to in the public domain as T-174, GI-262570, YM-440, MCC-555, JTT-501, AR-H039242, KRP-297, GW-409544, CRE-16336, AR-H049020, LY510929, MBX-102, CLX-0940, and GW-501516.

Additional examples of agents that could be co-administered with the compound(s) according to the invention are compounds for stimulating pancreatic beta-cell neogenesis and/or regeneration of islets. Examples of compounds currently used or in development which have a positive effect on islet number (i.e. beta-cells) include Byetta™ (exendin-4 inhibitor), vildagliptin (Galvus™, dipeptidylpeptidase inhibitor), Januvia™ (sitagliptin phosphate) and extracts from Gymnema sylvestrae leaf (Pharma Terra). The compound(s) according to the invention may also be administered with biomolecules related to cell regeneration such as β-cellulin, plant extracts from *Beta vulgaris* or *Ephedra herba*, and nicotinamide (see Banerjee et al. Rev Diabet Stud, 2005 2(3): 165-176).

Additional compounds or agents that may be used in accordance with the principles of the present invention are those capable of inducing pancreatic beta-cell growth or insulin producing cell growth and/or insulin production.

Such compounds include, but are not limited to: glucagon-like peptide-1 (GLP-1) and long-acting, DPP-IV-resistant GLP-1 analogs thereof, GLP-1 receptor agonists, gastric inhibitory polypeptide (GIP) and analogs thereof (e.g., which are disclosed in U.S. Patent Publication No. 2005/0233969), dipeptidyl peptidase IV (DPP-IV) inhibitors, insulin preparations, insulin derivatives, insulin-like agonists, insulin secretagogues, insulin sensitizers, biguanides, gluconeogenesis inhibitors, sugar absorption inhibitors, renal glucose re-uptake inhibitors, ß3 adrenergic receptor agonists, aldose reductase inhibitors, advanced glycation end products production inhibitors, glycogen synthase kinase-3 inhibitors, glycogen phosphorylase inhibitors, antilipemic agents, anorexic agents, lipase inhibitors, antihypertensive agents, peripheral circulation improving agents, antioxidants, diabetic neuropathy therapeutic agents, and the like.

Additional examples of agents that may be co-administered with the compound(s) according to the invention are anti-obesity agents, and appetite reducers. Examples of anti-obesity agents that can be used with the compounds according to the invention include Xenical™ (Roche), Meridia™ (Abbott), Acomplia™ (Sanofi-Aventis), and sympathomimetic phentermine. A non-limitative list of potentially useful known and emerging anti-obesity agents is set forth in Table 2 of WO 2006/131836, that table being incorporated herein by reference.

Additionally, the methods of the invention may also include co-administration of at least one other therapeutic agent for the treatment of another disease directly or indirectly related to diabetes and/or renal disorder complications, including but not limited to: dyslipidemia, hypertension, obesity, neuropathy, inflammation, and/or retinopathy, etc. Additional examples of agents that can be co-administered with the compound(s) according to the invention are corticosteroids; immunosuppressive medications; antibiotics; antihypertensive (such as ACE-inhibitors); diuretic medications; lipid lowering agents such as bile sequestrant resins, cholestyramine, colestipol, nicotinic acid, and more particularly drugs and medications used to reduce cholesterol and triglycerides (e.g., fibrates (e.g., Gemfibrozil®) and HMG-CoA inhibitors such as Lovastatin®, Atorvastatin®, Fluvastatin®, Lescol®@, Lipitor®, Mevacor®, Pravachol®, Pravastatin®, Simvastatin®, Zocor®, Cerivastatin®, etc); compounds that inhibit intestinal absorption of lipids (e.g., ezetiminde); nicotinic acid; and Vitamin D.

Additional examples of agents that can be co-administered with the compound(s) according to the invention are immunomodulating agents or immunosuppressants such as those that are used by Type 1 diabetics who have received an organ transplant.

Therefore, an additional aspect of the invention relates to methods of concomitant therapeutic treatment of a subject, comprising administering to a subject in need thereof an effective amount of a first agent and a second agent, wherein the first agent is as defined in Formula I, and the second agent is for the prevention or treatment of any one of the disorders or diseases indicated hereinbefore. As used herein, the term "concomitant" or "concomitantly" as in the phrases "concomitant therapeutic treatment" or "concomitantly with" includes administering a first agent in the presence of a second agent. A concomitant therapeutic treatment method includes methods in which the first, second, third or additional agents are co-administered. A concomitant therapeutic treatment method also includes methods in which the first or additional agents are administered in the presence of a second or additional agent(s), wherein the second or additional agent(s), for example, may have been previously administered. A concomitant therapeutic treatment method may be executed step-wise by different actors. For example, one actor may administer to a subject a first agent and as a second actor may administer to the subject a second agent and the administering steps may be executed at the same time, or nearly the same time, or at distant times, so long as the first agent (and/or additional agents) are after administration in the presence of the second agent (and/or additional agents). The actor and the subject may be the same entity (e.g., a human).

Accordingly, the invention also relates to a method for preventing, reducing or eliminating a symptom or complication of any one of the above-mentioned diseases or conditions (e.g., diabetes, etc). The method comprises administering, to a subject in need thereof, a first pharmaceutical composition comprising at least one compound of the invention and a second pharmaceutical composition comprising one or more additional active ingredients, wherein all active ingredients are administered in an amount sufficient to inhibit, reduce, or eliminate one or more symptoms or complications of the disease or condition to be treated. In one aspect, the administration of the first and second pharmaceutical composition is temporally spaced apart by at least about two minutes. Preferably the first agent is a compound of Formula I as defined herein, or a pharmaceutically acceptable salt thereof, e.g., sodium salt. The second agent may be selected from the list of compounds given hereinbefore.

Kits

The compound(s) of the invention may be packaged as part of a kit, optionally including a container (e.g., packaging, a box, a vial, etc.). The kit may be commercially used according to the methods described herein and may include instructions for use in a method of the invention. Additional kit components may include acids, bases, buffering agents, inorganic salts, solvents, antioxidants, preservatives, or metal chelators. The additional kit components are present as pure compositions, or as aqueous or organic solutions that incorporate one or more additional kit components. Any or all of the kit components optionally further comprise buffers.

The compound(s) of the invention may or may not be administered to a patient at the same time or by the same route of administration. Therefore, the methods of the invention encompass kits which, when used by the medical practitioner, can simplify the administration of appropriate amounts of two or more active ingredients to a patient.

A typical kit of the invention comprises a unit dosage form of at least one compound according to the invention, e.g., a compound Formula I as defined herein and a unit dosage form of at least one additional active ingredient. Examples of additional active ingredients that may be used in conjunction with the compounds of the invention include, but are not limited to, any of the compounds that could be used in combination with the compound(s) of the invention as indicated hereinbefore in the section "Co-administration".

Kits of the invention can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles are provided hereinbefore.

Assessment of Pancreas Function and Lipid Profiles

Quantitative assessment of pancreatic function and parameters of pancreatic diseases, pancreatic dysfunctions or pancreatic insufficiencies are well known in the art. Examples of assays for the determination of pancreas function/dysfunction includes evaluating at least one pancreatic function as assessed using biological and/or physiological parameters such as islets of Langerhans size, growth and/or secreting activity, beta-cells size, growth and/or secreting activity; insulin secretion and circulating blood levels, glucose blood levels, imaging of the pancreas, and pancreas biopsy. For instance, the examples in U.S. Pat. No. 5,424,286 describe methods for testing a compound stimulation of pancreatic insulin secretion, for testing a compound insulinotropic activity or for testing a compound activity on glycemia. Briscoe et al. (British Journal of Pharmacology, 2006, 148:619-628) disclose an insulin secretion assay using MIN6 cells.

Normal levels of glucose, insulin, plasma lipoprotein and/or triglycerides in human subjects are well known in the art and quantitative assessment of these biological parameters may also be useful for identifying subjects in need of treatments. Well known techniques commonly used by practitioners include measurement of fasting plasma glucose level and of plasma glucose levels in a glucose tolerance test, quantifying insulin resistance using the "hyperinsulinemic euglycemic clamp", testing bloodstream triglyceride levels after fasting 8 to 12 h, etc.

Diabetes Patient Selection and Monitoring

Typically a normal glomerular filtration rate (GFR) in humans is from about 100 to about 140 ml/min. In some embodiments, the subject is a human patient having advanced nephropathy (i.e. a GFR of under 75 ml/min). In some embodiments, the subject is a human patient having End Stage Renal Disease (ESRD) (i.e. GFR of less than 10 ml/min). In some embodiments, the methods, compounds or compositions of the invention are effective in increasing the patients' GFR value by at least 1, 5, 10, 15, 20 or 25, ml/min or more.

In some embodiments, the subject is at risk of or has been diagnosed with diabetes (e.g. type 1, type 2, maturity-onset diabetes of the young, latent autoimmune diabetes of adults (LADA), or gestational diabetes). In some embodiments, the compound(s) or composition(s) of the invention is administered in the early stages of onset of clinical symptoms of diabetes.

In some embodiments, the subject is hyperglycemic. In some embodiments, the subject's blood glucose levels are elevated, and the compound(s) and/or composition(s) of the invention are administered to a patient to restore normal levels. Normal levels of glucose are reported in medical treatises known to those of skill in the art. Typically blood sugar level is measured by means of a glucose meter, with the result either in mg/dL (milligrams per deciliter in the USA) or mmol/L (millimoles per liter in Canada and Europe) of blood. For example, the average normal person has a glucose level of around 4.5 to 7.0 mmol/L (80 to 125 mg/dL). In the diabetic patient a before-meal level of <6.1 mmol/L (<110 mg/dL) and a level two hours after the start of a meal of <7.8 mmol/L (<140 mg/dL) is acceptable. In some embodiments according to the invention, the subject blood glucose levels are above 150 mg/dl, or 175 mg/dl, or 200 mg/dl, or 225 mg/dl, or above 250 mg/dl, or over 300 mg/dl.

In some embodiments, the subject is a human patient with type 2 diabetes. As is known, type 2 diabetes results from a combination of insulin resistance and impaired insulin secretion, but ultimately many people with type 2 diabetes show markedly reduced pancreatic beta-cell mass and function which, in turn, causes type 2 diabetic patients to have a "relative" deficiency of insulin because pancreatic beta-cells are producing insufficient insulin to adequately allow glucose into cells to produce energy. Uncontrolled type 2 diabetes leads to excess glucose in the blood, resulting in hyperglycemia, or high blood sugar. A person with type 2 diabetes experiences fatigue, increased thirst, frequent urination, dry, itchy skin, blurred vision, slow healing cuts or sores, more infections than usual, numbness and tingling in feet. In some embodiments, the methods, compounds or compositions of the invention are effective in improving, curing and/or alleviating one or more of those symptoms.

In some embodiments, the compound(s) or composition(s) of the invention is administered in the early stages when the subject begins to show elevated glucose levels or increased beta-cell dysfunction, but before complete beta-cell failure. The compound(s) or composition(s) of the invention may also be administered when loss of beta-cell mass appears to be reversible.

In some embodiments, the subject is a human patient with type 1 diabetes. As is known, type 1 diabetes occurs when a person's immune system attacks the insulin producing beta-cells in the pancreas and destroys them such that the pancreas then produces little or no insulin. The most common type 1 diabetes symptoms include excessive thirst (polydipsia), frequent urination (polyuria), extreme hunger (polyphagia), extreme fatigue, and weight loss. In some embodiments, the methods, compounds or compositions of the invention are effective in improving, curing and/or alleviating one or more of those symptoms. In some embodiments, the subject as an autoimmune reaction leading to the destruction and/or apoptosis of beta-cells. In some embodiments, ketones are present in the urine of the subject. The compound(s) or composition(s) of the invention may also be administered when there are early signs of inflammation (e.g. cellular immune response, over production of cytokines (e.g. TNF-alpha, IFN-gamma, IL-1, IL-2 and IL-8). In some embodiments, the administration of the compound(s) or composition(s) of the invention can be initiated (a) before a subject who is at risk for an insulin related disorder, shows clinical symptoms of an insulin related disorder; (b) after the subject begins to show signs of an insulin related disorder, e.g., elevated glucose levels or beta-cell failure (as evidenced, e.g., by an increase or decrease of more than 5, 10, 20, or 30% in glucose levels or beta-cell failure compared to a reference value, e.g., a control, e.g., a non-disease state control); (c) when an insulin related disease, e.g., diabetes or another insulin related disorder described herein is diagnosed; (d) before, during or after a treatment for an insulin related disorder, e.g., diabetes, is begun or begins to exert its effects. The period over which the agent is administered (or the period over which clinically effective levels are maintained in the subject) can be long term, e.g., for six months or more or a year or more, or short term, e.g., for less than a year, six months, one month, two weeks or less.

In some embodiments, the compound(s) or composition(s) of the invention is administered before the subject shows clinical symptoms of a pancreatic disorder, but after a determination that the subject is at risk of pancreatic disorder, e.g., the subject is obese, or the subject has a family history of pancreatic disorders (e.g., a parent, sibling or grandparent of the subject has a pancreatic disorder such as diabetes).

In some embodiments, the compound(s) or composition(s) of the invention is administered as a supplemental therapy for a pancreatic disorder, e.g., the agent is administered in addition to administration of insulin.

In some embodiments, the subject exhibits abnormal pancreatic function (e.g., the subject displays abnormal insulin secretion, the subject displays signs of insulin resistance, the subject has hyperinsulinemia or hyperglycemia, etc.).

In some embodiments, the method for the prevention and/or treatment of diabetes according to the present invention may comprises the step of identifying a desired patient or patient population, for instance identifying a patient having or at risk of diabetes using an immune marker, a genetic marker, a metabolic marker, or a combination thereof. The patients may be identified before, during or after beginning of the treatment.

Combination Therapy and Dosage

The method of the present invention comprises administering to a mammal, e.g., a human patient or animal in need thereof, a preventative- or therapeutically-effective amount of a compound or pharmaceutical composition as defined herein.

Most insulin dependent diabetic patients require insulin injection at least on a daily basis. Multiple doses per day of insulin are currently recommended to achieve an adequate control of the disease, and the insulin administration is indicated by results of frequent glucose monitoring, another activity which is required of a diabetes patient for optimal management of the disease, which is performed for example as often as five times daily. In yet another aspect, the invention relates to a method of reducing insulin usage in an insulin-deficient diabetic patient, the method including administering compound(s) or composition(s) of the invention. According to that embodiment, as a result of this administration, remission of diabetes is initiated, so that the standard dosage of insulin given to a diabetic patient prior to therapy is reduced, as determined by the level of blood glucose obtained by monitoring, for example, by self-monitoring by the patient, during and following treatment. Remission from diabetes due to successful treatment according to the invention may be indicated by a decreased fasting blood level of glucose, and by a decreased level and duration of elevated blood glucose in response to a dietary challenge of sugar consumption. In yet another related aspect, the invention relates to a method of improving insulin sensitivity and/or decreasing insulin resistance in a subject in need of insulin, the method including administering compound(s) or composition(s) of the invention. Thus, in a preferred embodiment, insulin delivery after administering the compound(s) or composition(s) of the invention is reduced to less that about 75%, or to less that about 50%, or to less that about 10% or to less that about 1%, compared to usage in the diabetic patient before administration of the compound(s) or composition(s) of the invention. In other preferred embodiments, insulin administration is reduced from, for example, five injections to two injections per day; from two injections to one injection per day; and from one to none, as indicated by data obtained from monitoring blood glucose levels.

In some embodiment, the methods of the invention further comprise the step of evaluating the subject for one or more of the following parameters: (1) insulin blood levels; (2) glucose blood levels; (3) body weight. For instance, in one embodiment, the method comprises monitoring the blood glucose level at intervals of about once per day or less than about once per day; and reiterating administering the composition to the patient with a dosage adjusted according to the patient's blood glucose level. One of ordinary skill in the art of pharmacology, when treating a diabetic patient, is familiar with adjusting insulin dosage to levels of blood glucose following fasting and under other physiological conditions.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. The invention is further illustrated by the following examples, which should not be construed as further limiting.

EXAMPLES

The examples set forth herein below provide exemplary methods for the preparation of certain representative compounds encompassed by Formula I. Some Examples provide exemplary uses of certain representative compounds of the invention. Also provided are exemplary methods for assaying the compounds of the invention for in vitro and/or in vivo efficacy.

Instrumentation:

All HPLC chromatograms and mass spectra were recorded on an HP 1100 LC-MS Agilent instrument using an analytical C18 column (250×4.6 mm, 5 microns) with a gradient over 3 min of 50-99% CH3CN—H2O with 0.01% TFA as the eluant followed by isocratic over 3 min and a flow of 2 mL/min.

Example 1: Experimental Procedures for the Preparation Certain Representative Compounds Compound I: Sodium 2-[3,5-Dipentylphenyl]acetate

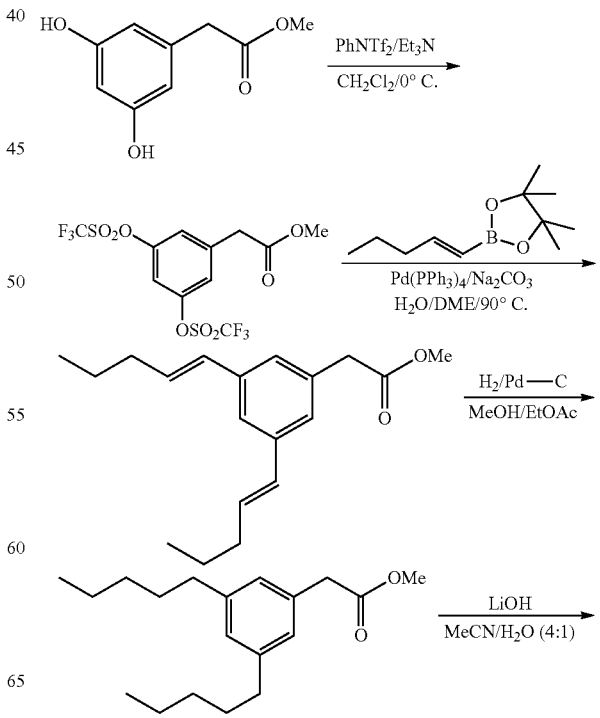

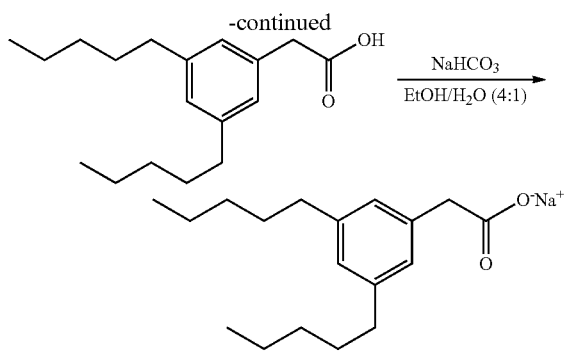

Step 1:

A suspension of methyl 2-[3,5-dihydroxyphenyl]acetate (1.00 g, 5.49 mmol) and N-phenyl-bis(trifluoromethylsulfonyl)imide (4.31 g, 12.1 mmol) in dichloromethane (20 ml), at 0° C. under nitrogen, was treated with triethylamine (1.68 ml, 12.1 mmol). A clear solution formed. The reaction was then stirred under nitrogen at 0° C. for 2 h, and at room temperature for 21 h. The reaction was diluted with ethyl acetate (100 ml), and the solution was washed with 0.5M aqueous sodium hydroxide (2×100 ml), and with saturated aqueous sodium chloride (75 ml); then dried over sodium sulphate; filtered and evaporated in vacuo to give the crude product. Purification on a Biotage™ 40 iM column (silica), eluting with ethyl acetate/hexane 0:1 to 1:9, gave methyl 2-[3,5-bis(trifluoromethylsulfonyloxy)phenyl]acetate (2.23 g, 91%) as pale oil. 1H NMR (400 MHz, CDCl3): δ 7.32 (d, J=2.2 Hz, 2H), 7.18 (dd, J=2.2, 2.2 Hz, 1H), 3.72 (s, 5H); 19F NMR (377 MHz, CDCl3): δ −73.20 (s, 3F); 13C NMR (101 MHz, CDCl3): δ 170.05, 149.48, 139.01, 122.95, 118.87 (q, JCF=320.5 Hz), 114.42, 52.62, 40.29.

Step 2:

A solution of the aryl bis(triflate) (2.23 g, 4.99 mmol) and (E)-1-penten-1-ylboronic acid pinacol ester (2.45 g, 12.5 mmol) in 1,2-dimethoxyethane (25 ml) was treated with a solution of sodium carbonate (1.59 g, 15.0 mmol) in water (8 ml). The solution was deoxygenated with nitrogen, and was then treated with Tetrakis(triphenylphosphine) palladium (0.58 g, 0.50 mmol). The mixture was heated at 90° C., in a sealed tube for 17 h. The reaction was cooled to room temperature and was partitioned between ethyl acetate (200 ml) and 1M aqueous hydrochloric acid (150 ml). The organic phase was washed with 5% aqueous sodium bicarbonate (150 ml), and with saturated aqueous sodium chloride (150 ml); then dried over sodium sulphate; filtered, and evaporated in vacuo to give the crude product. Purification on a Biotage™ 40 iL column (silica), eluting with ethyl acetate/hexane 0:1 to 3:97, gave methyl 2-[3,5-di[(E)-1-pent-1-enyl]phenyl]acetate as an inseparable 10:4 mixture with excess (E)-1-penten-1-ylboronic acid pinacol ester (1.12 g, 61%). 1H NMR (400 MHz, CDCl3): δ 7.21 (s, 1H), 7.10 (d, J=1.3 Hz, 2H), 6.34 (d, J=15.8 Hz, 2H), 6.22 (dd, J=15.8, 6.7 Hz, 1H), 3.65 (s, 3H), 3.55 (s, 2H), 2.18 (tdd, J=6.8, 6.8, 1.0 Hz, 2H), 1.49 (qt, J=7.4, 7.2 Hz, 2H), 0.96 (t, J=7.4 Hz, 3H); 13C NMR (101 MHz, CDCl3): δ 172.04, 138.59, 134.47, 131.34, 129.97, 125.57, 122.75, 52.07, 41.32, 35.39, 22.77, 13.97.

Step 3:

A solution of the unsaturated compound (1.12 g, 78.5% w/w, 3.07 mmol) in ethyl acetate (1 ml) and methanol (1 ml) was treated with palladium on carbon (10% w/w Pd; 0.12 g). The mixture was degassed with hydrogen, and was stirred under 1 atm. of hydrogen at room temperature for 22 h. The reaction was filtered, and evaporated in vacuo to give methyl 2-[3,5-dipentylphenyl]acetate as an inseparable 10:4 mixture with pentylboronic acid pinacol ester (0.86 g, 76%). 1H NMR (400 MHz, CDCl3): δ 6.93 (s, 3H), 3.70 (s, 3H), 3.59 (s, 2H), 2.58 (t, J=7.9 Hz, 2H), 1.58-1.66 (m, 2H), 1.32-1.38 (m, 4H), 0.91 (t, J=6.8 Hz, 3H).

Step 4:

A solution of the methyl ester (0.86 g, 79% w/w, 2.34 mmol) in acetonitrile (24 ml) was treated with a solution of lithium hydroxide (0.28 g, 11.7 mmol) in water (6 ml), and the reaction was stirred at room temperature for 22 h. The reaction was quenched with 1M aqueous hydrochloric acid (55 ml), and then extracted with ethyl acetate (100 ml). The organic extract was washed with saturated aqueous sodium chloride (50 ml); then dried over sodium sulphate; filtered, and evaporated in vacuo to give the crude product. Purification on a SiliaSep™ silicon oxide column, eluting with ethyl acetate/hexane 0:1 to 1:4, gave 2-[3,5-dipentyl]phenyl]acetic acid as a colorless oil (0.55 g, 84%). 1H NMR (400 MHz, CDCl3): δ 6.99 (s, 3H), 3.65 (s, 2H), 2.63 (t, J=7.8 Hz, 2H), 1.64-71 (m, 2H), 1.36-1.44 (m, 4H), 0.97 (t, J=6.9 Hz, 3H); 13C NMR (101 MHz, CDCl3): δ 178.96, 143.55, 133.21, 127.93, 127.06, 41.47, 36.13, 31.94, 31.47, 22.86, 14.34.

Step 5.

A solution of the acid (0.48 g, 1.75 mmol) in ethanol (12 ml) was treated with a solution of sodium bicarbonate (0.15 g, 1.75 mmol) in water (3 ml), and the reaction was stirred at room temperature for 3 d. Ethanol was evaporated in vacuo, and the residual aqueous syrup was diluted with water (50 ml), filtered (PES, 0.2 µm), and lyophilised to give sodium 2-[3,5-dipentylphenyl]acetate as a white solid (0.52 g, quantitative). mp 225-230° C.; 1H NMR (400 MHz, CD3OD+D2O): δ 6.92 (s, 2H), 6.76 (s, 1H), 3.41 (s, 2H), 2.50 (t, J=7.5 Hz, 2H), 1.52-1.59 (m, 2H), 1.23-1.33 (m, 4H), 0.85 (t, J=6.9 Hz, 3H); 13C NMR (101 MHz, CD3OD+D2O): δ 179.99, 142.66, 137.63, 126.66, 126.16, 45.11, 35.61, 31.36, 31.19, 22.41, 13.47; LRMS (ESI): m/z 277.5 (w, [M−Na++2H+]), 231.1 (100%, tropylium ion from loss of carboxy group); HPLC: 3.0 min.

Compound II: Sodium Salt of 2-(3,5-Dihexylphenyl)acetic acid

The above compound was prepared from (E)-hex-1-enylboronic acid pinacol ester as for Compound I. White solid; 1H NMR (400 MHz, CD3OD): δ 6.96 (s, 2H), 6.79 (s, 1H), 3.43 (s, 2H), 2.54 (d, J=7.7 Hz, 4H), 1.55-1.63 (m, 4H), 1.28-1.36 (m, 12H), 0.89 (t, J=6.8 Hz, 6H); 13C NMR (101 MHz, CD3OD): δ 179.68, 142.38, 137.82, 126.55, 126.07, 45.30, 35.87, 31.83, 31.67, 29.02, 22.61, 13.42; LRMS (ESI): m/z 322.0 (100%, M−Na++H++NH4+) and 259.0 (35%, M−CO2Na); UPLC (System A): 8.9 min. UPLC System A: Mobile phase A=10 mM aqueous ammonium bicarbonate; mobile phase B=acetonitrile; solid phase=HSS T3 column; gradient=5-100% B in A over 10 minutes.

Compound III: Sodium Salt of 2-(2-Hydroxy-3,5-dipentylphenyl)acetic acid

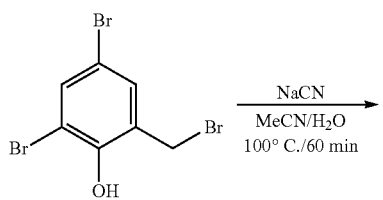

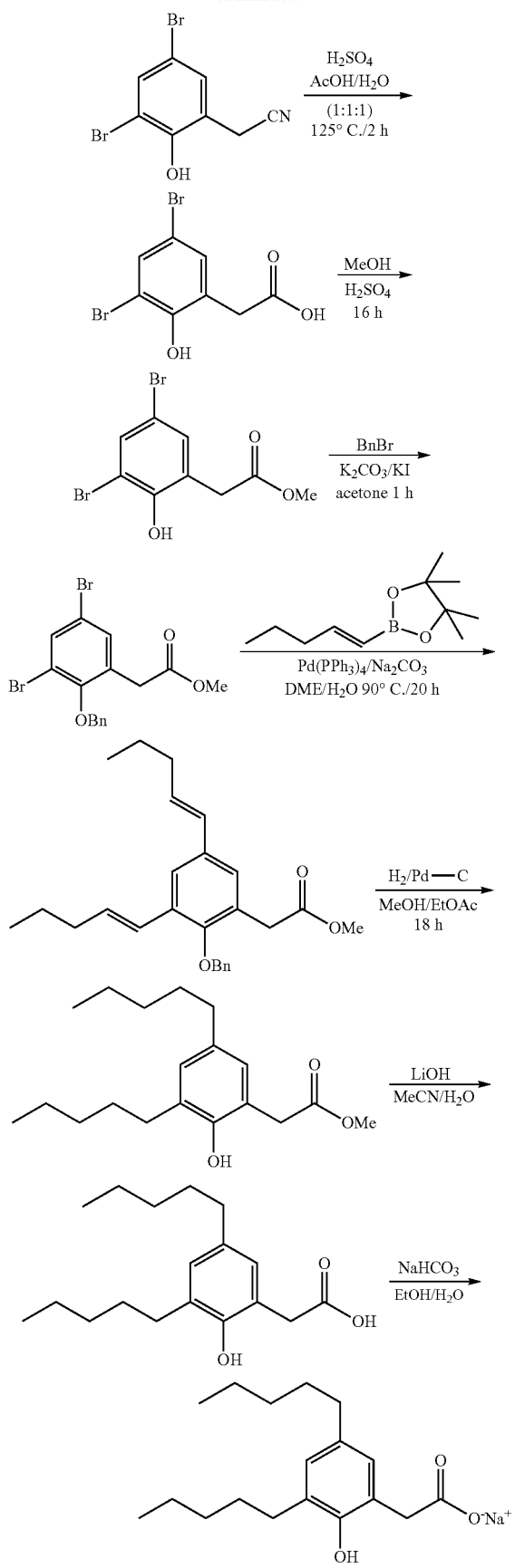

Step 1:

A solution of 2,4-dibromo-6-(bromomethyl)phenol (3.5 g, 10.0 mmol) in acetonitrile (17 ml) was treated with a solution of sodium cyanide (2.5 g, 50.0 mmol) and the reaction was heated at 100° C. under reflux for 1 h. The reaction mixture cooled to room temperature and was poured into water (100 ml). The pH was adjusted from 10 to 8 with 1M aqueous hydrochloric acid, and the mixture was extracted with ethyl acetate (3×250 ml). Combined extracts were washed with 1M aqueous hydrochloric acid (250 ml) and with saturated aqueous sodium chloride (250 ml); dried over sodium sulfate; filtered and evaporated in vacuo to give the crude product. Extraction with acetone; filtration; and evaporation in vacuo gave 2-(3,5-dibromo-2-hydroxyphenyl)acetonitrile (2.6 g, 90%). 1H NMR (400 MHz, d6-acetone): δ 8.75 (br s, 1H), 7.69 (d, J=2.3 Hz, 1H), 7.54 (d, J=2.3 Hz, 1H), 3.92 (s, 2H); 13C NMR (101 MHz, d6-acetone): δ 151.31, 134.51, 131.92, 122.80, 117.43, 111.89, 111.53, 18.70.

Step 2:

2-(3,5-Dibromo-2-hydroxyphenyl)acetonitrile (2.6 g, 9.0 mmol) was treated with a mixture of sulfuric acid (2.5 ml), acetic acid (2.5 ml) and water (2.5 ml), and the reaction was heated at 125° C. under reflux for 2 h. The reaction mixture was cooled to room temperature and was poured into a mixture of ice (50 ml) and water (50 ml), and was then stirred until the ice had melted. The mixture was extracted with ethyl acetate (250 ml); and the extract was then washed with water (100 ml) and with saturated aqueous sodium chloride (100 ml); dried over sodium sulfate; filtered and evaporated in vacuo to give the crude 2-(3,5-dibromo-2-hydroxyphenyl)acetic acid (3.1 g). This material was used directly in the next step without further purification or characterization.

Step 3:

A solution of crude 2-(3,5-dibromo-2-hydroxyphenyl)acetic acid (3.1 g, 9.0 mmol) in methanol (17 ml) was treated with sulfuric acid (0.43 ml, 8.1 mmol) and the reaction was stirred at ambient temperature for 16 h. Methanol was evaporated in vacuo, and the residue was dissolved in ethyl acetate (270 ml). The solution was washed with water (2×200 ml) and with saturated aqueous sodium chloride (130 ml); dried over sodium sulfate; filtered and evaporated in vacuo to give the crude product. Purification on a Biotage™ SP1 system (120 g silica cartridge), eluting with 0-20% ethyl acetate in hexanes, gave methyl 2-(3,5-dibromo-2-hydroxyphenyl)acetate (1.4 g, 49%). 1H NMR (400 MHz, CDCl3): δ 7.52 (d, J=2.2 Hz, 1H), 7.23 (d, J=2.2 Hz, 1H), 6.42 (br s, 1H), 3.72 (s, 3H), 3.65 (s, 2H); 13C NMR (101 MHz, CDCl3): δ 172.06, 150.60, 133.74, 133.50, 123.94, 112.62, 111.77, 52.78, 36.61.

Step 4:

A solution of methyl 2-(3,5-dibromo-2-hydroxyphenyl)acetate (0.5 g, 1.54 mmol) in acetone (5 ml) was treated with potassium carbonate (0.26 g, 1.86 mmol), potassium iodide (0.05 g, 0.32 mmol) and benzyl bromide (0.20 ml, 1.7 mmol), and the reaction was stirred at room temperature for 1 h. Acetone was evaporated in vacuo, and the residue was partitioned between ethyl acetate (50 ml) and 1M aqueous hydrochloric acid (50 ml). The organic phase was washed with saturated aqueous sodium chloride (50 ml); dried over sodium sulfate; filtered and evaporated in vacuo to give the crude product. Purification on a Biotage™ SP1 system (40 g silica cartridge), eluting with 0-10% ethyl acetate in hexanes, gave methyl 2-(2-(benzyloxy)-3,5-dibromophenyl)acetate (0.6 g, 95%). 1H NMR (400 MHz, CDCl3): δ 7.67 (d, J=2.4 Hz, 1H), 7.48-7.51 (m, 2H), 7.37 (d, J=2.4 Hz, 1H), 7.34-7.43 (m, 3H), 4.99 (s, 2H), 3.66 (s, 3H), 3.60 (s, 2H); 13C NMR (101 MHz, CDCl3): δ 171.26, 153.79, 136.56, 135.38, 133.57, 132.04, 128.82, 128.64, 128.52, 118.69, 117.56, 75.53, 52.50, 35.86.

Step 5:

Methyl 2-(2-(benzyloxy)-3,5-dibromophenyl)acetate (0.3 g, 0.73 mmol) and (E)-pent-1-enylboronic acid pinacol ester (0.4 g, 1.79 mmol) were coupled as for Compound I, step 2, to give methyl 2-(2-(benzyloxy)-3,5-di((E)-pent-1-enyl)phenyl)acetate (0.21 mg, 72%). 1H NMR (400 MHz, CDCl3): δ 7.50 (d, J=7.2 Hz, 2H), 7.44 (dd, J=7.2, 7.2 Hz, 2H), 7.43 (d, J=2.1 Hz, 1H), 7.38 (dd, J=7.2, 7.2 Hz, 1H), 7.18 (d, J=2.1 Hz, 1H), 6.72 (d, J=15.8 Hz, 1H), 6.39 (d, J=15.8 Hz, 1H), 6.32 (dt, J=15.8, 7.0 Hz, 1H), 6.22 (dt, J=15.8, 6.8 Hz, 1H), 4.87 (s, 2H), 3.69 (s, 3H), 3.67 (s, 2H), 2.20-2.29 (m, 4H), 1.50-1.60 (m, 4H), 1.01 (t, J=7.3 Hz, 3H), 1.00 (t, J=7.4 Hz, 3H); 13C NMR (101 MHz, CDCl3): δ 172.49, 153.59, 137.58, 134.35, 132.91, 131.91, 130.84, 129.53, 128.78, 128.32, 128.30, 128.24, 127.26, 125.21, 123.89, 75.89, 52.21, 35.94, 35.74, 35.42, 22.87, 22.77, 14.07, 14.06.

Step 6:

Methyl 2-(2-(benzyloxy)-3,5-di((E)-pent-1-enyl)phenyl)acetate (0.2 g, 0.53 mmol) was hydrogenated as for Compound I, step 3, to give methyl 2-(2-hydroxy-3,5-dipentylphenyl)acetate (0.12 g, 73%). 1H NMR (400 MHz, CDCl3): δ 7.37 (s, 1H), 6.92 (d, J=2.1 Hz, 2H), 6.77 (d, J=2.1 Hz, 1H), 3.76 (s, 3H), 3.67 (s, 2H), 2.65 (t, J=7.8 Hz, 2H), 2.51 (t, J=7.8 Hz, 2H), 1.58-1.66 (m, 4H), 1.31-1.41 (m, 8H), 0.93 (t, J=7.0 Hz, 3H), 0.92 (t, J=6.9 Hz, 3H); 13C NMR (101 MHz, CDCl3): δ 175.01, 151.27, 135.14, 131.48, 129.92, 128.52, 120.30, 52.95, 38.35, 35.34, 32.15, 31.86, 31.74, 30.61, 30.03, 22.87, 22.83, 14.34, 14.31.

Step 7:

Methyl 2-(2-hydroxy-3,5-dipentylphenyl)acetate (0.2 g, 0.53 mmol) was hydrolysed as for Compound I, step 4, to give the crude product mixed with lactonised material. A small portion was purified on a Biotage™ SP1 system (120 g silica cartridge), eluting with 0-100% ethyl acetate in hexanes, to give 2-(2-hydroxy-3,5-dipentylphenyl)acetic acid (13.5 mg). 1H NMR (400 MHz, CDCl3): δ 10.5 (br s, 1H), 6.89 (d, J=2.2 Hz, 1H), 6.78 (d, J=2.2 Hz, 1H), 6.32 (br s, 1H), 3.66 (s, 2H), 2.58 (t, J=7.9 Hz, 2H), 2.48 (t, J=7.8 Hz, 2H), 1.52-1.63 (m, 4H), 1.26-1.37 (m, 8H), 0.90 (t, J=7.0 Hz, 3H), 0.88 (t, J=6.8 Hz, 3H).

Step 8:

2-(2-Hydroxy-3,5-dipentylphenyl)acetic acid (13.5 mg, 0.046 mmol) was converted to the sodium salt as for Compound I, step 5 to give sodium 2-(2-hydroxy-3,5-dipentylphenyl)acetate (11 mg, 77%). 1H NMR (400 MHz, CD3OD): δ 6.72 (d, J=2.0 Hz, 1H), 6.69 (d, J=2.0 Hz, 1H), 3.46 (s, 2H), 2.56 (t, J=7.6 Hz, 2H), 2.44 (t, J=7.6 Hz, 2H), 1.50-1.61 (m, 4H), 1.25-1.37 (m, 8H), 0.90 (t, J=6.8 Hz, 3H), 0.88 (t, J=7.0 Hz, 3H); 13C NMR (101 MHz, CD3OD): δ 180.33, 151.94, 133.47, 130.37, 128.21, 127.81, 123.99, 42.90, 34.97, 31.81, 31.60, 31.40, 30.25, 29.88, 22.51, 22.45, 13.29, 13.24; LRMS (ESI negative): m/z 291.2 (100%, M−Na+); UPLC (System B): 7.7 min. UPLC System B: Mobile phase A=0.1% aqueous formic acid; mobile phase B=0.1% formic acid in acetonitrile; solid phase=HSS T3 column; gradient=5-100% B in A over 10 minutes.

Compound IV: Sodium Salt of 2-(3,5-Dihexyl-2-hydroxyphenyl)acetic acid

The above compound was prepared as for Compound III, using (E)-hex-1-enylboronic acid pinacol ester. 1H NMR (400 MHz, CD3OD): δ 6.72 (d, J=2.0 Hz, 1H), 6.69 (d, J=2.0 Hz, 1H), 3.46 (s, 2H), 2.56 (t, J=7.6 Hz, 2H), 2.44 (t, J=7.5 Hz, 2H), 1.50-1.60 (m, 4H), 1.27-1.37 (m, 12H), 0.89 (t, J=6.6 Hz, 3H), 0.88 (t, J=6.80 Hz, 3H); LRMS (ESI negative): m/z 319 (100%, M−Na+); UPLC (System B): 8.7 min. ULC System B: Mobile phase A=0.1% aqueous formic acid; mobile phase B=0.1% formic acid in acetonitrile; solid phase=HSS T3 column; gradient=5-100% B in A over 10 minutes.

Compound V: Sodium Salt of 2-(4-Hydroxy-3,5-dipentylphenyl)acetic acid

The above compound was prepared as for Compound III, from 2-(3,5-dibromo-4-hydroxyphenyl)acetic acid. 1H NMR (400 MHz, CD3OD): δ 6.87 (s, 2H), 3.33 (s, 2H), 2.55 (t, J=7.7 Hz, 4H), 1.53-1.61 (m, 4H), 1.31-1.37 (m, 8H), 0.90 (t, J=7.0 Hz, 6H); LRMS (ESI negative): m/z 291.1 (100%, M−Na+); UPLC (System B): 6.8 min. UPLC System B: Mobile phase A=0.1% aqueous formic acid; mobile phase B=0.1% formic acid in acetonitrile; solid phase=HSS T3 column; gradient=5-100% B in A over 10 minutes.

Compound VI: Sodium Salt of 2-(3,5-Dihexyl-4-hydroxyphenyl)acetic acid

The above compound was prepared as for Compound III, from 2-(3,5-dibromo-4-hydroxyphenyl)acetic acid, and (E)-hex-1-enylboronic acid pinacol ester. 1H NMR (400 MHz, CD3OD): δ 6.72 (d, J=2.0 Hz, 1H), 6.69 (d, J=2.0 Hz, 1H), 3.46 (s, 2H), 2.56 (t, J=7.6 Hz, 2H), 2.44 (t, J=7.5 Hz, 2H), 1.50-1.60 (m, 4H), 1.27-1.37 (m, 12H), 0.89 (t, J=6.6 Hz, 3H), 0.88 (t, J=6.8 Hz, 3H); LRMS (ESI negative): m/z 319.1 (100%, M−Na+); UPLC (System B): 7.6 min. UPLC System B: Mobile phase A=0.1% aqueous formic acid; mobile phase B=0.1% formic acid in acetonitrile; solid phase=HSS T3 column; gradient=5-100% B in A over 10 minutes.

Compound VII: Sodium Salt of 2-(4-Fluoro-3,5-dihexylphenyl)acetic acid

The above compound was prepared as for Compound III, starting from 3,5-dibromo-4-fluorobenzyl bromide and (E)-hex-1-enylboronic acid pinacol ester. 3,5-Dibromo-4-fluorobenzyl bromide was prepared by bromination of 3,5-dibromo-4-fluorotoluene with N-bromosuccinimide and azobisisobutyronitrile in acetonitrile at 80° C. 1H NMR (400 MHz, CD3OD): δ 6.98 (d, JHF=7.0 Hz, 2H), 3.38 (s, 2H), 2.57 (t, J=7.7 Hz, 4H), 1.54-1.61 (m, 4H), 1.28-1.37 (m, 12H), 0.89 (t, J=6.7 Hz, 6H); 19F NMR (377 MHz, CD3OD): δ −132.17 (d, JHF=6.6 Hz, 1F); 13C NMR (101 MHz, CD3OD): δ 179.44, 158.11 (d, JCF=239.8 Hz), 133.26 (d, JCF=3.8 Hz), 128.73 (d, JCF=5.4 Hz), 128.56 (d, JCF=16.9 Hz), 44.52, 31.69, 30.35 (d, JCF=1.5 Hz), 28.98, 28.97 (d, JCF=3.1 Hz), 22.51, 13.29; LRMS (ESI negative): m/z 321.0 (100%, M−Na+); UPLC (System B): 9.2 min. UPLC System B: Mobile phase A=0.1% aqueous formic acid; mobile phase B=0.1% formic acid in acetonitrile; solid phase=HSS T3 column; gradient=5-100% B in A over 10 minutes.

Compound VIII: Sodium Salt of 2-(4-Fluoro-3,5-dipentylphenyl)acetic acid

The above compound was prepared as for Compound III, starting from 3,5-dibromo-4-fluorobenzyl bromide. 1H NMR (400 MHz, CD3OD): δ 6.98 (d, JHF=6.8 Hz, 2H), 3.37 (s, 2H), 2.57 (t, J=7.6 Hz, 4H), 1.54-1.62 (m, 4H), 1.28-1.37 (m, 8H), 0.90 (t, J=7.0 Hz, 6H); 19F NMR (377 MHz, CD3OD): δ −132.34 (d, JHF=6.6 Hz, 1F); 13C NMR (101 MHz, CD3OD): δ 179.41, 158.10 (d, JCF=239.8 Hz), 133.26 (d, JCF=3.8 Hz), 128.72 (d, JCF=4.6 Hz), 128.56 (d, JCF=16.9 Hz), 44.51, 31.54, 30.07, 28.92 (d, JCF=3.1 Hz), 22.38, 13.22; LRMS (ESI negative): m/z 293.0 (100%, M−Na+); UPLC (System B): 8.4 min. UPLC System B: Mobile phase A=0.1% aqueous formic acid; mobile phase B=0.1% formic acid in acetonitrile; solid phase=HSS T3 column; gradient=5-100% B in A over 10 minutes.

Compound IX: Sodium Salt of 2-(2-Benzyl-3,5-dipentylphenyl)acetic Acid

The title compound was prepared as for Compound I, from methyl 2-(2-benzyl-3,5-di((E)-pent-1-enyl)phenyl)acetate. The latter was isolated as a side product (1.1% yield) from the scale-up of Compound I. $^1$H NMR (400 MHz, CD$_3$OD): δ 7.17 (dd, J=7.3, 7.3 Hz, 2H), 7.09 (dd, J=7.3, 7.3 Hz, 1H), 6.97-6.99 (m, 3H), 6.86 (d, J=1.8 Hz, 1H), 4.13 (s, 2H), 3.40 (s, 2H), 2.55 (t, J=7.7 Hz, 2H), 2.49 (t, J=7.8 Hz, 2H), 1.59-1.67 (m, 2H), 1.31-1.45 (m, 6H), 1.21-1.26 (m, 4H), 0.91 (t, J=7.0 Hz, 3H), 0.82 (t, J=7.0 Hz, 3H); $^{13}$C NMR (101 MHz, CD$_3$OD): δ 179.48, 141.46, 141.24, 140.47, 137.46, 133.70, 128.36, 128.05, 127.86, 127.75, 125.42, 43.25, 35.54, 33.90, 33.61, 31.86, 31.65, 31.25, 30.96, 22.49, 22.40, 13.31, 13.23; LRMS (ESI negative): m/z 365.0 (20%, M−Na$^+$), 321.1 (100%, M−CO$_2$Na); UPLC (System B): 9 min. (UPLC System B: Mobile phase A=0.1% aqueous formic; mobile phase B=0.1% formic in acetonitrile; solid phase=HSS T3; gradient=5-100% B in A over 10 min.

Compound X: Sodium 2-[3,5-Di[(E)-Pent-1-enyl]phenyl]acetate

The title compound was prepared using the same procedure as for Compound I, but with the omission of the hydrogenation step. Mp 226-30° C.; $^1$H NMR (400 MHz, CD$_3$OD): δ 7.18 (d, J=1.2 Hz, 2H), 7.11 (d, J=1.2 Hz, 1H), 6.34 (d, J=15.9 Hz, 2H), 2.23 (dt, J=15.9, 6.7 Hz, 2H), 3.44 (s, 2H), 2.14-2.19 (m, 4H), 1.49 (tq, J=7.4, 7.4 Hz, 4H), 0.95 (t, J=7.3 Hz, 6H); $^{13}$C NMR (101 MHz, CD$_3$OD): δ 179.41, 138.34, 138.06, 130.30, 130.16, 125.26, 121.60, 45.24, 35.10, 22.55 & 12.98; LRMS (negative mode): m/z 271 (w, [M−Na$^+$]), 227.2 (100%, [M−Na$^+$−CO$_2$]); UPLC: 8 min. (UPLC; Conditions solvent A=0.1% formic acid in water; Solvent B=0.1% formic acid in acetonitrile; Gradient: 5-100% B in A over 10 m in at 0.7 ml/min.)

Compound XI: Sodium 3-[3,5-Dipentylphenyl]propanoate

The title compound was prepared using the same procedure as for Compound I starting from 3-[3,5-dibromophenyl]propanoic acid. mp 211-217° C.; $^1$H NMR (400 MHz, CDCl$_3$): δ 6.73 (s, 1H), 6.68 (s, 2H), 2.73-2.77 (m, 2H), 2.42-2.46 (m, 2H), 2.38 (t, J=7.8 Hz, 4H), 1.43-1.51 (m, 4H), 1.19-1.28 (m, 8H), 0.83 (t, J=6.9 Hz, 6H); $^{13}$C NMR (101 MHz, CDCl$_3$): δ 182.55, 142.93, 141.85, 125.96, 125.77, 39.80, 36.13, 32.77, 31.99, 31.47, 22.79 & 14.27; LRMS (negative mode): m/z 289.4 (100%, [M−Na$^+$]); UPLC: 9 min. (UPLC: Conditions solvent A=0.1% formic acid in water, solvent B=0.1% formic acid in acetonitrile, Gradient: 5-100% B in A over 10 min at 0.7 ml/min.

Compound XII: Sodium Salt of 2-(3,5-Di((E)-hex-1-enyl)phenyl)acetic acid

The title compound was prepared in the same manner as compound II, but with the omission of the hydrogenation step. Off-white solid: $^1$H NMR (400 MHz, CD$_3$OD): δ 7.17 (d, J=1.1 Hz, 2H), 7.10 (s, 1H), 6.33 (d, J=15.8 Hz, 2H), 6.22 (dt, J=15.8, 6.7 Hz, 2H), 3.44 (s, 2H), 2.16-2.21 (m, 4H), 1.34-1.46 (m, 8H), 0.93 (t, J=7.3 Hz, 6H); $^{13}$C NMR (101 MHz, CD$_3$OD): δ 179.44, 138.34, 138.07, 130.37, 130.13, 125.27, 121.60, 45.26, 32.70, 31.67, 22.19, 13.27; LRMS (ESI negative mode): m/z 299.2 (m, M−Na$^+$) and 255.2 (100%, M−Na$^+$−CO$_2$); UPLC: 8.7 min. (UPLC conditions solvent A=0.1% formic acid in water; mobile phase B=0.1% formic acid in acetonitrile; solid phase=HSS T3; gradient=5-100% B in A over 10 min).

Compound XIII: Sodium Salt of 2-(2-Fluoro-3,5-dipentylphenyl)acetic Acid

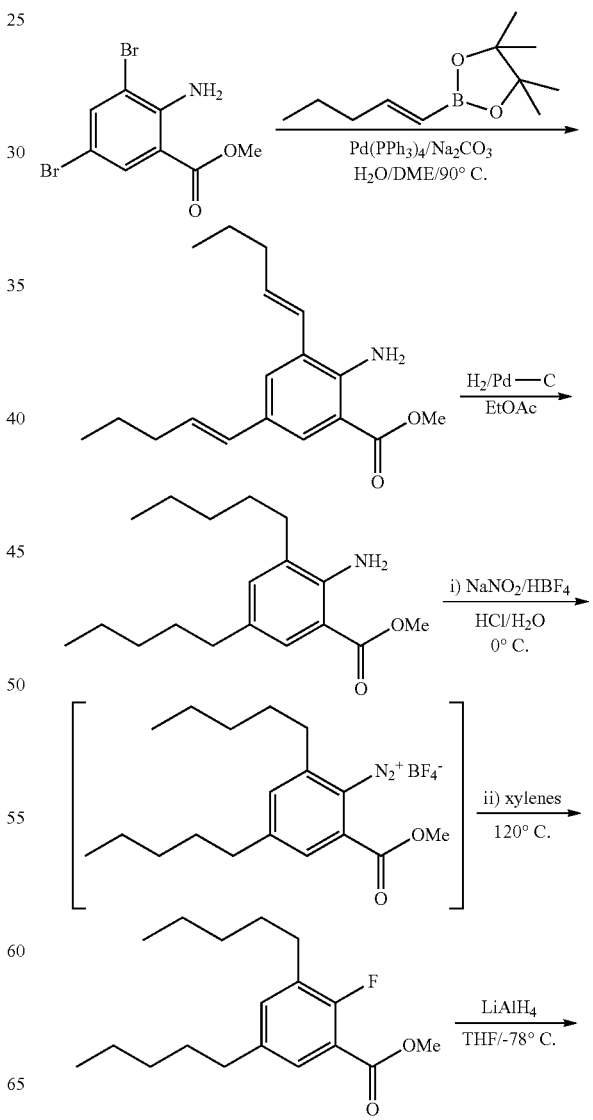

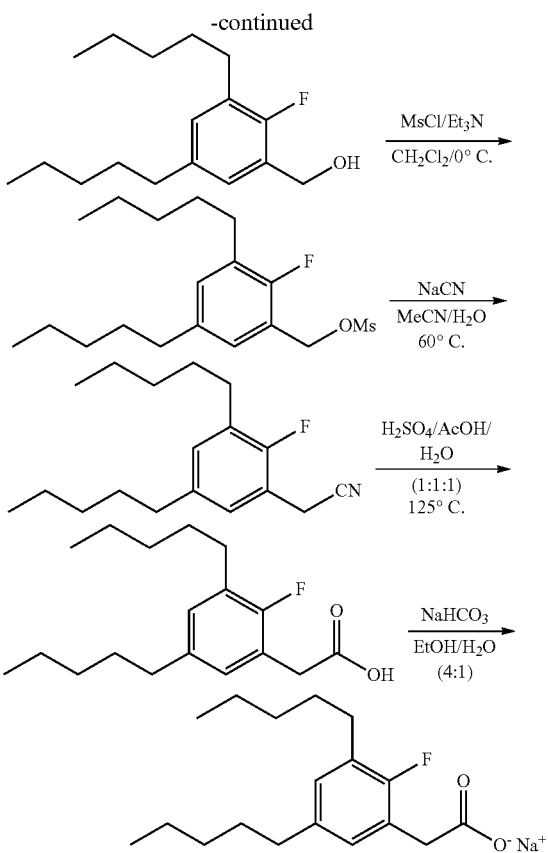

Step 1:
Methyl 2-amino-3,5-dibromobenzoate (10.0 g, 32.4 mmol) was coupled with (E)-1-penten-1-ylboronic acid pinacol ester (15.2 g, 77.7) using the method described for compound I to give methyl 2-amino-3,5-di[(E)-pent-1-enyl]benzoate (6.00 g, 64%). 1H NMR (400 MHz, CDCl3): δ 7.76 (d, J=2.2 Hz, 1H), 7.37 (d, J=2.2 Hz, 1H), 6.35 (d, J=15.4 Hz, 1H), 6.26 (d, J=15.8 Hz, 1H), 6.08 (dt, J=15.6, 7.0 Hz, 1H), 6.06 (dt, J=15.8, 7.0 Hz, 1H), 5.5-6.5 (br s, 2H), 3.87 (s, 3H), 2.19-2.25 (m, 2H), 2.13-2.18 (m, 2H), 1.43-1.56 (m, 8H), 0.97 (t, J=7.3 Hz, 3H), 0.94 (t, J=7.3 Hz, 3H).

Step 2:
Methyl 2-amino-3,5-di[(E)-pent-1-enyl]benzoate (5.7 g, 19.9 mmol) was hydrogenated as described for compound I to give methyl 2-amino-3,5-dipentylbenzoate (5.50 g, 95%). 1H NMR (400 MHz, CDCl3): δ 7.50 (d, J=2.2 Hz, 1H), 6.95 (d, J=2.2 Hz, 1H), 5.5-6.1 (br s, 2H), 3.79 (s, 3H), 2.40 (t, J=7.2 Hz, 4H), 1.45-1.58 (m, 4H), 1.20-1.32 (m, 8H), 0.84 (t, J=7.2 Hz, 3H), 0.82 (t, J=7.1 Hz, 3H).

Step 3:
Methyl 2-amino-3,5-dipentylbenzoate (4.5 g, 15.4 mmol) was treated with aqueous tetrafluoroboric acid (5.5M, 3.7 ml, 20 mmol) and aqueous hydrochloric acid (8.5M, 3.3 ml, 28 mmol). The mixture was cooled to 0° C., and was then treated dropwise with an aqueous solution of sodium nitrite (2.1M, 8.8 ml, 18.5 mmol) over 2 minutes. After 60 minutes at 0° C., the reaction mixture was extracted with xylenes (30 ml). The xylenes extract was dried over sodium sulfate, and was then heated from 60° C. to 120° C. over 55 minutes. Filtration and evaporation of xylenes in vacuo gave the crude compound, which was purified on a SiliaSep SiO2 column, eluting with ethyl acetate in hexanes (0-5%) to give methyl 2-fluoro-3,5-dipentylbenzoate (3.1 g, 69%). 1H NMR (400 MHz, CDCl3): δ 7.50 (dd, JHF=6.5 Hz, JHH=2.4 Hz, 1H), 7.15 (dd, JHF=6.5 Hz, JHH=2.4 Hz, 1H), 3.91 (s, 3H), 2.62 (td, JHH=7.7 Hz, JHF=1.2 Hz, 2H), 2.56 (t, J=7.7 Hz, 2H), 1.55-1.63 (m, 4H), 1.26-1.37 (m, 8H), 0.89 (t, J=7.0 Hz, 6H); 19F NMR (377 MHz, CDCl3): δ −121.31 (dd, JHF=6.6, 6.6 Hz, 1F).

Step 4.
A solution of methyl 2-fluoro-3,5-dipentylbenzoate (3.1 g, 10.6 mmol) in anhydrous tetrahydrofuran (60 ml) was cooled to −78° C., and was treated slowly with lithium aluminium hydride (0.5 g, 13.8 mmol). The reaction mixture was stirred at −78° C. for 25 minutes, then at 0° C. for 30 minutes. The reaction was quenched by addition of ethyl acetate. The mixture was washed with aqueous potassium sodium tartrate (1M, 100 ml), and with saturated aqueous sodium chloride (100 ml); and was then dried over sodium sulfate, filtered and evaporated in vacuo to give the crude compound. Purification on a SiliaSep SiO2 column, eluting with ethyl acetate in hexanes (3-20%) gave 2-fluoro-3,5-dipentylbenzyl alcohol (1.8 g, 65%). 1H NMR (400 MHz, CDCl3): δ 7.02 (dd, JHF=6.8 Hz, JHH=2.3 Hz, 1H), 6.92 (dd, JHF=7.1 Hz, JHH=2.4 Hz, 1H), 4.71 (s, 2H), 2.59 (td, JHH=7.6 Hz, JHF=1.2 Hz, 2H), 2.54 (t, J=7.8 Hz, 2H), 1.73 (s, 1H), 1.54-1.62 (m, 4H), 1.25-1.36 (m, 8H), 0.894 (t, J=7.0 Hz, 3H), 0.890 (t, J=7.1 Hz, 3H); 19F NMR (377 MHz, CDCl3): δ −131.25 (dd, JHF=6.7, 6.6 Hz, 1F); 13C NMR (101 MHz, CDCl3): δ 157.41 (d, JCF=242.9 Hz), 138.48 (d, JCF=4.3 Hz), 130.07 (d, JCF=5.4 Hz), 129.33 (d, JCF=16.2 Hz), 127.33 (d, JCF=15.6 Hz), 126.67 (d, JCF=4.6 Hz), 59.84 (d, JCF=5.4 Hz), 35.50, 31.86, 31.77, 31.62, 30.21, 29.21 (d, JCF=2.4 Hz), 22.80, 22.74, 14.28 (2C).

Step 5:
A solution of 2-fluoro-3,5-dipentylbenzyl alcohol (1.4 g, 5.3 mmol) in anhydrous dichloromethane (35 ml) was cooled to 000° C., and was treated dropwise with methanesulfonyl chloride (0.5 ml, 5.8 mmol) over 10 minutes. The reaction was stirred at 0° C. for 20 minutes, and was then quenched by addition of ice-cold water (35 ml). The organic phase was washed with aqueous hydrochloric acid (1M, 35 ml), saturated aqueous sodium bicarbonate (35 ml) and with saturated aqueous sodium chloride (35 ml); and was then dried over sodium sulfate, filtered and evaporated in vacuo to give the crude 2-fluoro-3,5-dipentylbenzyl methanesulfonate (1.7 g, 93%). This material was used in the next step without purification. 1H NMR (400 MHz, CDCl3): δ 7.02-7.05 (m, 2H), 5.26 (d, JHF=1.0 Hz, 2H), 2.98 (s. 3H), 2.52-2.63 (m, 2H), 2.54 (t, J=7.8 Hz, 2H), 1.54-1.62 (m, 4H), 1.27-1.37 (m, 8H), 0.892 (t, J=7.0 Hz, 3H), 0.888 (t, J=7.0 Hz, 3H).

Step 6:
The pH of a solution of sodium cyanide (0.4 g, 7.4 mmol) in water (5 ml) was adjusted to pH 10 with 6M aqueous hydrochloric acid. A solution of 2-fluoro-3,5-dipentylbenzyl methanesulfonate (1.7 g, 4.9 mmol) in acetonitrile (25 ml) was then added, and the reaction was heated at 60° C. for 2 h. The reaction mixture was concentrated to 15 ml in vacuo, and was extracted with ethyl acetate (100 ml). The organic extract was washed with water (100 ml), and with saturated aqueous sodium chloride (100 ml); and was then dried over sodium sulfate, filtered and evaporated in vacuo to give the crude compound. Purification on a SiliaSep SiO2 column, eluting with ethyl acetate in hexanes (1-10%) gave 2-[2-fluoro-3,5-dipentylphenyl]acetonitrile (0.7 g, 55%). 1H NMR (400 MHz, CDCl3): δ 7.04 (dd, JHF=6.9 Hz, JHH=2.2 Hz, 1H), 6.96 (dd, JHF=7.1 Hz, JHH=2.2 Hz, 1H), 3.72 (s, 2H), 2.59 (td, JHH=7.7 Hz, JHF=0.9 Hz, 2H), 2.55 (t, J=7.8 Hz, 2H), 1.54-1.62 (m, 4H), 1.27-1.37 (m, 8H), 0.90 (t, J=7.0 Hz, 6H); 19F NMR (377 MHz, CDCl3): δ −131.25 (ddd, JHF=7.0, 7.0, 0.8 Hz, 1F); 13C NMR (101 MHz, CDCl3): δ 157.02 (d, JCF=244.5 Hz), 139.16 (d, JCF=4.7 Hz), 130.84 (d, JCF=4.6 Hz), 129.93 (d, JCF=16.1 Hz), 126.97 (d, JCF=3.1 Hz), 117.52, 116.79 (d, JCF=16.2

Hz), 35.38, 31.74, 31.66, 31.54, 30.06, 29.16 (d, JCF=2.4 Hz), 22.74, 22.68, 17.90 (d, JCF=6.1 Hz), 14.26, 14.23.

Step 7:

A mixture of 2-[2-fluoro-3,5-dipentylphenyl]acetonitrile (0.7 g, 2.7 mmol), acetic acid (4 ml) and water (4 ml) was treated dropwise with concentrated sulfuric acid (4 ml); and the mixture was then heated at 125° C. for 3.5 h. The reaction was cooled to room temperature and was then quenched by addition of ice (40 ml). The mixture was extracted with ethyl acetate (40 ml), and the organic extract was then washed with saturated aqueous sodium chloride (40 ml); dried over sodium sulfate, filtered and evaporated in vacuo to give 2-[2-fluoro-3,5-dipentylphenyl]acetic acid (537 mg, 67%). 1H NMR (400 MHz, CDCl3): δ 6.84 (dd, JHF=7.0 Hz, JHH=2.3 Hz, 1H), 6.80 (dd, JHF=6.8 Hz, JHH=2.2 Hz, 1H), 3.59 (d, JHF=1.2 Hz, 2H), 2.52 (t, J=7.5 Hz, 2H), 2.45 (t, J=7.8 Hz, 2H), 1.46-1.55 (m, 4H), 1.20-1.30 (m, 8H), 0.80-0.84 (m, 6H).

Step 8:

2-[2-Fluoro-3,5-dipentylphenyl]acetic acid (537 mg, 1.8 mmol) was converted to the sodium salt as described for compound I to give sodium 2-[2-fluoro-3,5-dipentylphenyl]acetate (465 mg, 81%) as a pale brown, sticky solid: 1H NMR (400 MHz, CD3OD): δ 6.94 (dd, JHF=6.9 Hz, JHH=2.2 Hz, 1H), 6.83 (dd, JHF=7.0 Hz, JHH=2.3 Hz, 1H), 3.48 (d, JHF=1.1 Hz, 2H), 2.58 (t, J=7.6 Hz, 2H), 2.51 (t, J=7.6 Hz, 2H), 1.54-1.62 (m, 4H), 1.28-1.38 (m, 8H), 0.90 (t, J=7.0 Hz, 3H), 0.89 (t, J=7.0 Hz, 3H); 19F NMR (377 MHz, CD3OD): δ -130.71 (dd, JHF=6.6, 6.6 Hz, 1F); 13C NMR (101 MHz, CD3OD): δ 178.31, 157.95 (d, JCF=240.6 Hz), 137.64 (d, JCF=3.8 Hz), 128.72 (d, JCF=4.6 Hz), 128.42 (d, JCF=17.7 Hz), 128.21 (d, JCF=5.4 Hz), 124.50 (d, JCF=17.7 Hz), 37.94 (d, JCF=3.1 Hz), 35.05, 31.52, 31.45, 31.37, 30.00, 28.96 (d, JCF=2.3 Hz), 22.43, 22.38, 13.23, 13.21; LRMS (ESI negative mode): m/z 293 (w, M−Na+) and 249.1 (100%, M−Na+−CO2); UPLC: 8.4 min (UPLC conditions Mobile phase A=0.1% formic acid in water; mobile phase B=0.1% formic acid in acetonitrile; solid phase=HSS T3; gradient=5-100% B in A over 10 min.

Compound XIV: Sodium Salt of 2-(3,5-Dipentylphenyl)-2-methylpropanoic Acid

The above compound was prepared in the same manner as compound I, with the additional step of alkylation of the methyl 2-[3,5-dipentylphenyl]acetate intermediate with sodium hydride and methyl iodide; and with the temperature of the ester hydrolysis step being raised to 100° C. Off-white solid: 1H NMR (400 MHz, CD3OD): δ 7.04 (d, J=1.3 Hz, 2H), 6.76 (s, 1H), 2.54 (t, J=7.7 Hz, 4H), 1.55-1.63 (m, 4H), 1.46 (s, 6H), 1.27-1.38 (m, 8H), 0.90 (t, J=7.0 Hz, 6H); 13C NMR (101 MHz, CD3OD): δ 184.58, 148.51, 141.98, 125.57, 123.46, 36.02, 48.26, 31.59, 31.42, 27.57, 22.47, 13.29; LRMS (ESI negative mode): m/z 303.1 (100%, M−Na+); UPLC: 8.9 min (UPLC conditions mobile phase A=0.1% formic acid in water; mobile phase B=0.1% formic acid in acetonitrile; solid phase=HSS T3; gradient=5-100% B in A over 10 min).

Example 2: In Vitro Effect of Compounds on Insulin Production in Beta Cells (β-TC-6 Cells)

β-TC-6 cells where used to determine if compounds according to the present invention were able to induce the production of insulin with or without stimulation with glucose. Briefly, β-TC-6 cells (200,000 cells/ml) were incubated in DMEM media and 15% heat inactivated serum in presence of absence of glucose (0.8M) with/without Compound I for 30 minutes and further incubated for 2 hours with a solution of Krebs containing 2.5, 11 and 25 mM glucose. Supernatants were collected and used for the detection of insulin (ELISA) performed as recommended by the supplier.

As shown in Table 1, glucose-induced insulin production in β-TC-6 cells is increased with Compound I in presence of glucose only.

As shown in Table 2, Compounds of the present invention increase glucose-induced insulin production in β-TC-6 under stimulation of 11 mM glucose as compared to the control.

TABLE 1

Effect of Compound I on glucose-induced insulin secretion by β-TC-6 cells

| Glucose | Compound I | % Control | Average | Standard Deviation |
|---|---|---|---|---|
| — | — | 100.00 | 100.00 | 0.00 |
| | | 100.00 | | |
| | | 100.00 | | |
| | | 100.00 | | |
| | | 100.00 | | |
| | | 100.00 | | |
| | 80 μM | 79.57 | 100.75 | 48.47 |
| | | 38.71 | | |
| | | 70.97 | | |
| | | 123.28 | | |
| | | 114.63 | | |
| | | 177.33 | | |
| | 40 μM | 53.76 | 101.46 | 45.53 |
| | | 86.02 | | |
| | | 47.31 | | |
| | | 155.22 | | |
| | | 135.63 | | |
| | | 130.81 | | |
| 11 mM | — | 109.17 | 100.00 | 9.46 |
| | | 87.16 | | |
| | | 103.67 | | |
| | | 110.46 | | |
| | | 98.03 | | |
| | | 91.51 | | |
| | 80 μM | 192.66 | 174.37 | 30.84 |
| | | 174.31 | | |
| | | 203.67 | | |
| | | 145.51 | | |
| | | 129.29 | | |
| | | 200.78 | | |
| | 40 μM | 195.41 | 160.45 | 24.66 |
| | | 187.16 | | |
| | | 135.78 | | |
| | | 149.35 | | |
| | | 151.88 | | |
| | | 143.13 | | |

TABLE 2

Effect of several Compounds on glucose-induced insulin secretion by β-TC-6 cells

| Compound | Structure | Insulin (ng/ml) |
|---|---|---|
| Control | | 53 |
| I | 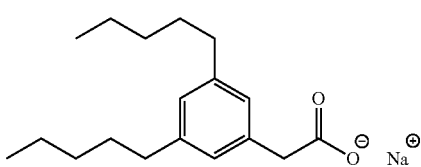 [SMILES: CCCCCc1cc(CCCCC)cc(CC(=O)[O-])c1 ; [Na+]] | 76 |

TABLE 2-continued

Effect of several Compounds on glucose-induced insulin secretion by β-TC-6 cells

| Compound | Structure | Insulin (ng/ml) |
|---|---|---|
| II | 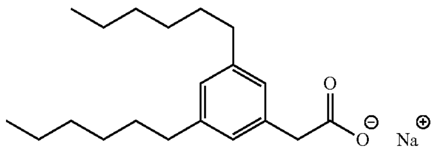 [SMILES: CCCCCCc1cc(CCCCCC)cc(CC(=O)[O-])c1 ; [Na+]] | 123 |
| III | 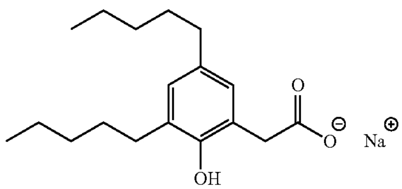 [SMILES: CCCCCc1cc(CCCCC)c(O)c(CC(=O)[O-])c1 ; [Na+]] | 109 |
| IV | 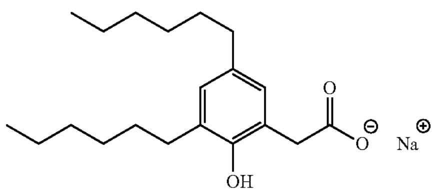 [SMILES: CCCCCCc1cc(CCCCCC)c(O)c(CC(=O)[O-])c1 ; [Na+]] | 147 |
| V | 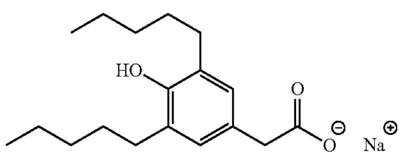 [SMILES: CCCCCc1cc(CC(=O)[O-])cc(CCCCC)c1O ; [Na+]] | 59 |
| VI | 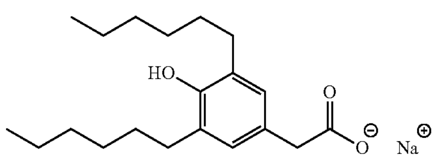 [SMILES: CCCCCCc1cc(CC(=O)[O-])cc(CCCCCC)c1O ; [Na+]] | 67 |
| VIII | 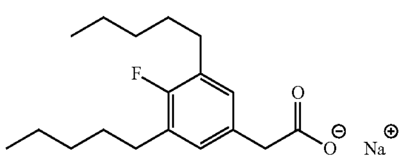 [SMILES: CCCCCc1cc(CC(=O)[O-])cc(CCCCC)c1F ; [Na+]] | 64 |
| IX | 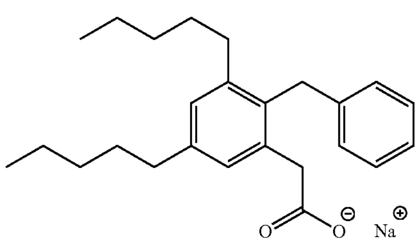 [SMILES: CCCCCc1cc(CCCCC)c(Cc2ccccc2)c(CC(=O)[O-])c1 ; [Na+]] | 110 |
| X | 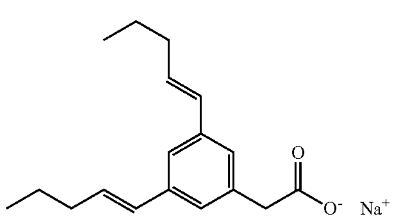 [SMILES: CCC/C=C/c1cc(/C=C/CCC)cc(CC(=O)[O-])c1 ; [Na+]] | 102 |
| XI | | 89 |
| XII | | 70 |

Example 3: In Vivo Effect of Compound I on Glucose Concentration in Diabetic db/db Mice Demonstration of the in vivo effect of Compound I was measured in the diabetic mouse (db/db) model using the following procedure. Male Lepr db (db/db) and age- and sex-matched control mice with the same genetic background (C57BL/6) were used. Animals were randomized using blood sugar measurement (5-hours starved) at week 6 and uninephrectomy (removal of right kidney) was performed. Sham animals (C57BL/6) underwent exposition of the right kidney. Animals that underwent the sham operation were given vehicle (saline) and were used as negative controls. C57BL/6 mice that were uninephrectomized were given vehicle and were used as positive controls. Db/db mice were treated with oral administration of compound I at 10 and 50 mg/kg per day for 105 days. Serum glucose was measured every two to four weeks.

FIG. 1 represents the percent increase of blood glucose level of C57BL/6, db/db uninephrectomized (NX) mice and with treatment with Compound I compared to C57BL/6 sham mice (negative control, 100%). Db/db mice had a high increasing level of blood sugar compared to C57BL/6 uninephrectomized or sham. Treatment with Compound I at a concentration of 10 mg/kg reduces blood glucose compare to NX db/db but stay stable over time, however at 50 mg/kg Compound I induces a significant decrease in blood glucose to a normal level.

Figure 2:
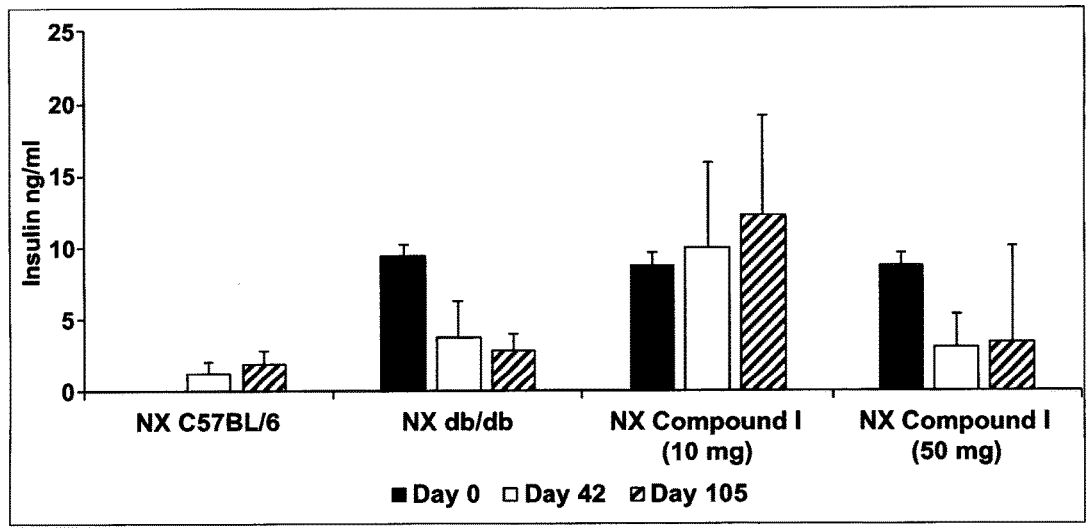
FIG. 2 is a bar graph showing that Compound I reverses the fall of insulin secretion in uninephrectomized db/db mice, according to Example 3.

FIG. 2 represents the hyperinsulenemia of the db/db uninephrectomized (NX) mice compared to the normal insulin level of C57BL/6 mice. In fact, insulin level is high in young db/db mice, and with time, this level of insulin decreased with a high blood glucose level (FIG. 1) followed by death. Treatment with Compound I at 10 mg/kg keeps a high insulin level (stabilization compare to Day 0) and a decrease in blood glucose level (FIG. 1) compared to NX db/db. Furthermore, at higher concentration (50 mg/kg), Compound I reduces the insulin level close to a normal level. Moreover, in these animals treated with 50 mg/kg of Compound I the blood sugar is at a normal level (FIG. 1).

Figure 3:
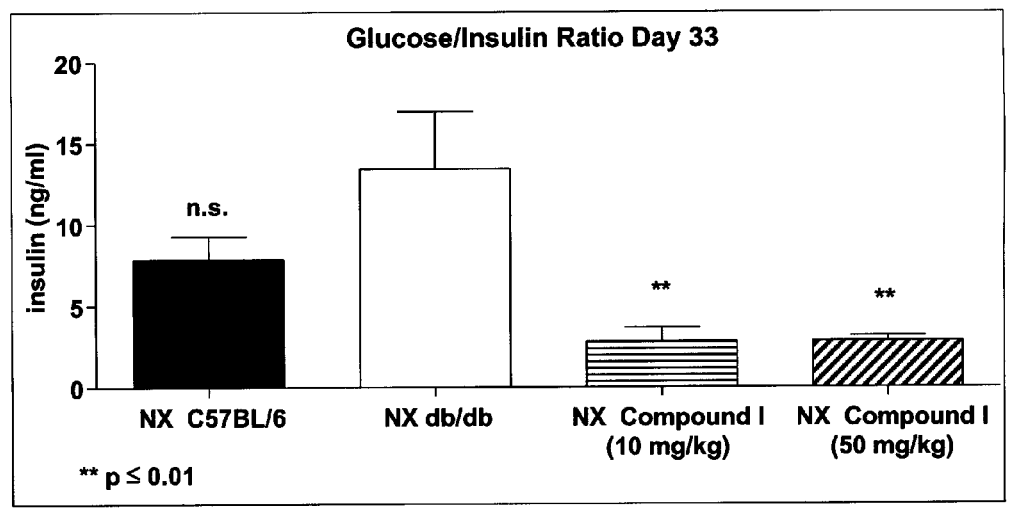
FIG. 3 is a bar graph showing effect of Compound I on the Glucose/Insulin Ratio at Day 33 in uninephrectomized db/db mice, according to Example 3.
Figure 4:
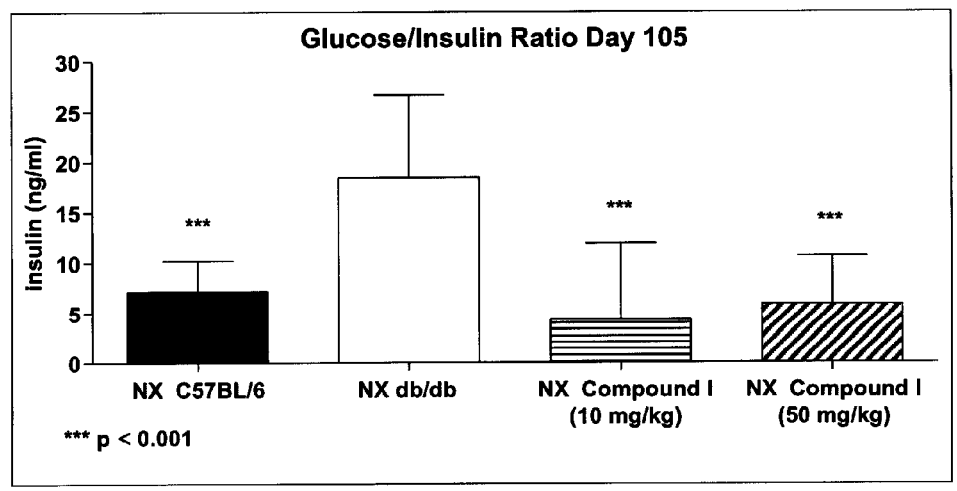
FIG. 4 is a bar graph showing effect of Compound I on the Glucose/Insulin Ratio at Day 105 in uninephrectomized db/db mice, according to Example 3.

The glucose/insulin ratio is used to demonstrate insulin resistance. FIGS. 3 and 4 represent the effect of Compound 1 (early and late-sustained effect, day 33 and 55 respectively) on insulin resistance. Db/db mice are well recognized to have high insulin resistance as demonstrated by a high ratio of glucose/insulin. Treatment with Compound 1 reduces the glucose/insulin ratio, both at day 33 and day 105, indicating a reduction in insulin resistance.

Figure 5A:
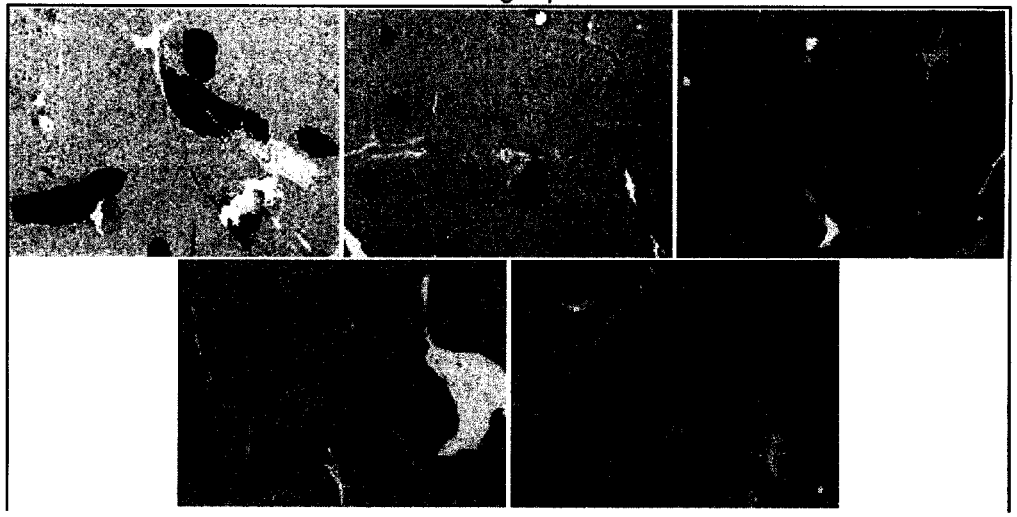
FIGS. 5A-5D are panels with pictures showing detection of insulin in pancreatic islets of normal mice (C57BL/6), and of diabetic mice (db/db) with and without Compound I (10 or 50 mg/kg) according to Example 3.
Figure 5B:
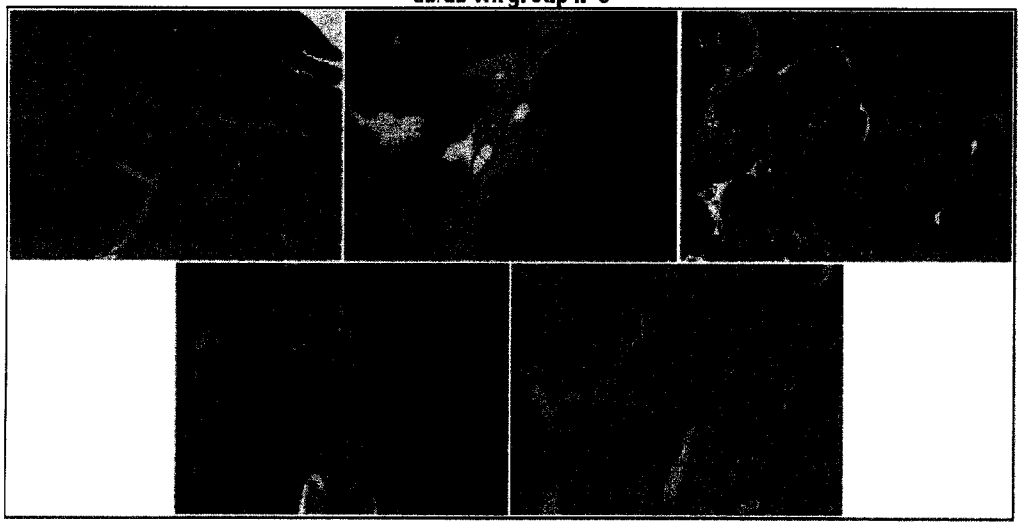
Figure 5C:
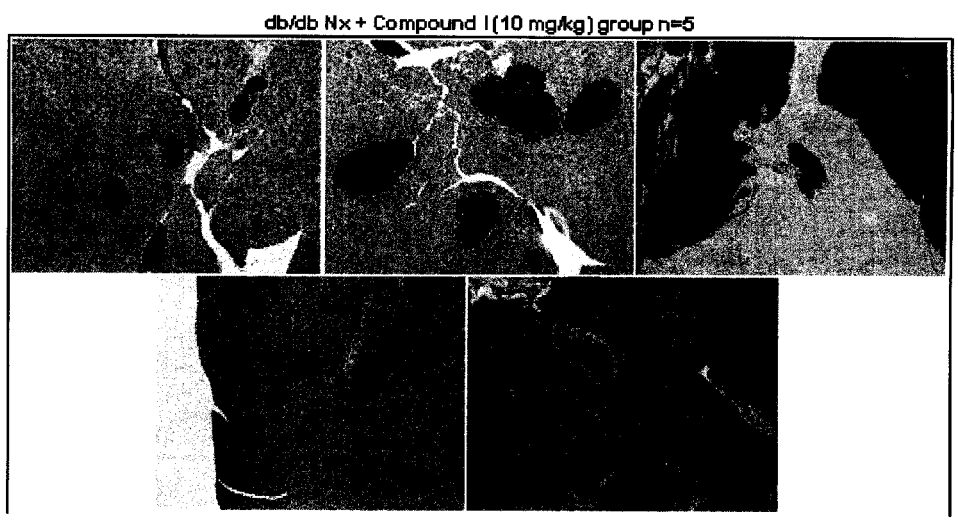
Figure 5D:
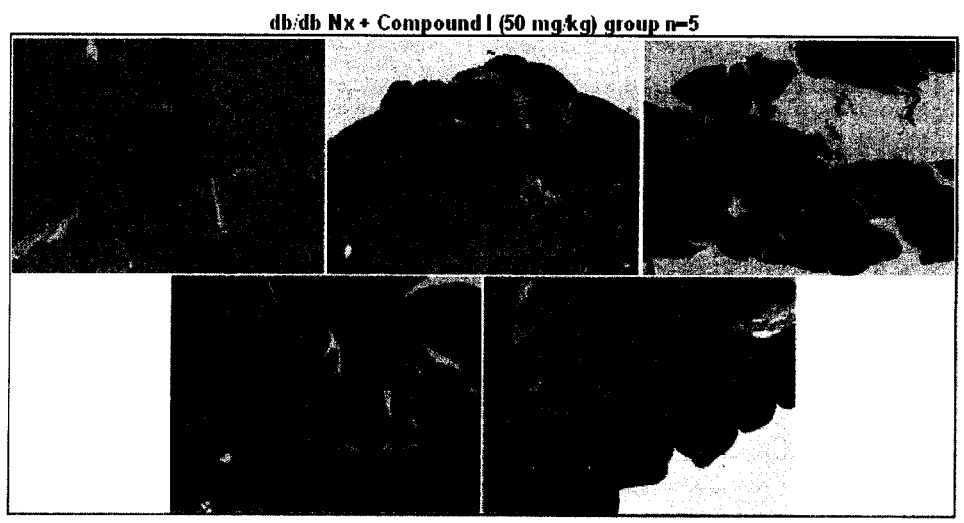

The pictures of FIGS. 5A-5D show histoimmunostaining of insulin (brown-dark) in the pancreatic islets. As demonstrated, a strong reduction in insulin detection is observed in the pancreatic islets of diabetic db/db mice (FIG. 5B) when compared to the normal islets of the C57BL/6 mice (FIG. 5A; normal non-diabetic mice). Treatment with Compound 1, at both concentrations, reverses the loss of insulin detection indicating that Compound 1 protects and/or regenerates the pancreatic islets (FIG. 5C and FIG. 5D).

Example 4: In Vivo Effect of Compound I on Blood Triglycerides Levels

Figure 6:
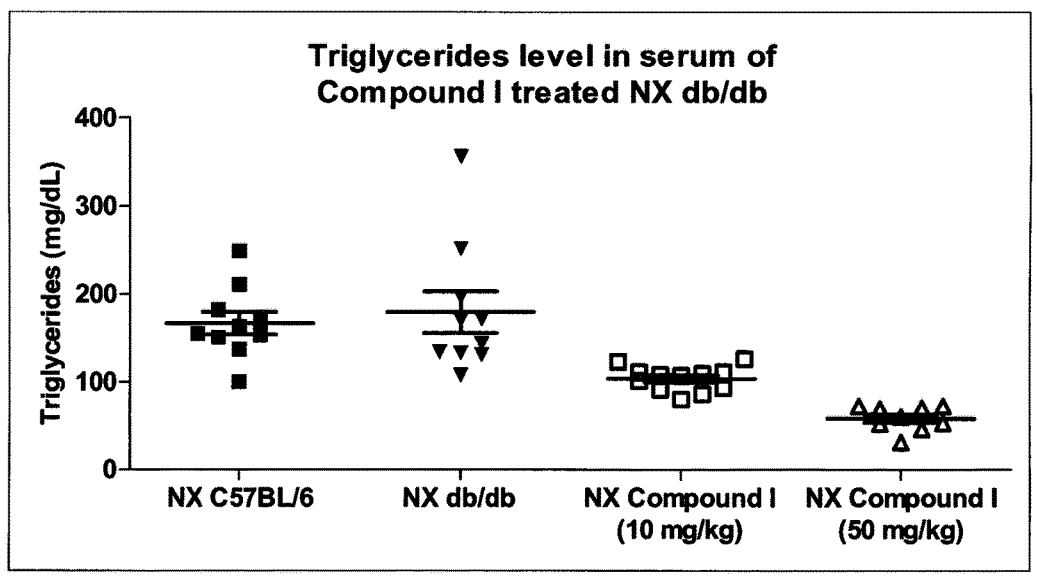
FIG. 6 is a dot graph showing triglycerides level in serum of uninephrectomized db/db mice treated or not with Compound I (10 or 50 mg/kg), according to Example 4.

It is known that blood triglycerides is often associated with diabetes. High triglyceride levels in the blood tend to coexist with low levels of HDL ("good") cholesterol, contributing to a condition called diabetic dyslipidemia. It is also known that a combination of high triglycerides, low HDL and central obesity are the hallmarks of the metabolic syndrome, which occurs in a majority people with type 2 diabetes. FIG. 6 illustrates that Compound I reduced the blood triglyceride level in serum of uninephrectomized db/db mice. These results suggest a positive role of the compounds according to the invention for reducing blood triglyceride levels in vivo and suggest a positive role in the prevention and/or treatment of triglyceride-related diseases or conditions such as diabetic dyslipidemia and metabolic syndrome.

Headings are included herein for reference and to aid in locating certain sections These headings are not intended to limit the scope of the concepts described therein, and these concepts may have applicability in other sections throughout the entire specification Thus, the present invention is not intended to be limited to the embodiments shown herein but is to be accorded the widest scope consistent with the principles and novel features disclosed herein.

The singular forms "a", "an" and "the" include corresponding plural references unless the context clearly dictates otherwise.

Unless otherwise indicated, all numbers expressing quantities of ingredients, reaction conditions, concentrations, properties, and so forth used in the specification and claims are to be understood as being modified in all instances by the term "about". At the very least, each numerical parameter should at least be construed in light of the number of reported significant digits and by applying ordinary rounding techniques. Accordingly, unless indicated to the contrary, the numerical parameters set forth in the present specification and attached claims are approximations that may vary depending upon the properties sought to be obtained. Notwithstanding that the numerical ranges and parameters setting forth the broad scope of the embodiments are approximations, the numerical values set forth in the specific examples are reported as precisely as possible. Any numerical value, however, inherently contain certain errors resulting from variations in experiments, testing measurements, statistical analyses and such.

It is understood that the examples and embodiments described herein are for illustrative purposes only and that various modifications or changes in light thereof will be suggested to persons skilled in the art and are to be included within the present invention and scope of the appended claims.

The invention claimed is:

1. A method for preventing and/or treating diabetes selected from Type I diabetes, Type II diabetes, Type III diabetes (Alzheimer), and gestational diabetes, said method comprising the step of administering to a subject in need thereof a compound represented by Formula I or a pharmaceutically acceptable salt thereof, at a dose of 0.1 to 5 mg/kg per day; wherein Formula I is:

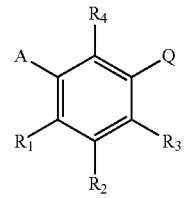

Formula I wherein
A is $C_5$ alkyl, $C_6$ alkyl, $C_5$ alkenyl, $C_6$ alkenyl, C(O)—$(CH_2)_n$—$CH_3$ or CH(OH)—$(CH_2)_n$—$CH_3$ wherein n is 3 or 4;
$R_1$ is H, F or OH;
$R_2$ is $C_5$ alkyl, $C_6$ alkyl, $C_5$ alkenyl, $C_6$ alkenyl, C(O)—$(CH_2)_n$—$CH_3$ or CH(OH)—$(CH_2)_n$—$CH_3$ wherein n is 3 or 4;
$R_3$ is H, F, OH or $CH_2Ph$;
$R_4$ is H, F or OH;
Q is
1) $(CH_2)_mC(O)OH$ wherein m is 1 or 2,
2) $CH(CH_3)C(O)OH$,
3) $C(CH_3)_2C(O)OH$,
4) $CH(F)$—$C(O)OH$,
5) $CF_2$—$C(O)OH$, or
6) $C(O)$—$C(O)OH$.

2. The method of claim 1, wherein the dose is 0.1 to 1.0 mg/kg per day.

3. The method of claim 1, wherein A is $C_5$ alkyl, $C_6$ alkyl, $C_5$ alkenyl, or $C_6$ alkenyl.

4. The method of claim 1, wherein $R_2$ is $C_5$ alkyl, $C_6$ alkyl, $C_5$ alkenyl, or $C_6$ alkenyl.

5. The method of claim 1, wherein $R_3$ is H, OH or $CH_2Ph$.

6. The method of claim 1, wherein $R_4$ is H.

7. The method of claim 1, wherein Q is $(CH_2)_mC(O)OH$, and wherein m is 1 or 2.

8. The method of claim 1, wherein Q is $(CH_2)_mC(O)OH$, and wherein m is 1.

9. The method of claim 1, wherein:
A is $C_5$ alkyl, $C_6$ alkyl, $C_5$ alkenyl, or $C_6$ alkenyl;
$R_1$ is H or OH;
$R_2$ is $C_5$ alkyl, $C_6$ alkyl, $C_5$ alkenyl, or $C_6$ alkenyl;
$R_3$ is H, OH or $CH_2Ph$;
$R_4$ is H; and
Q is $(CH_2)_mC(O)OH$ wherein m is 1 or 2.

10. The method of claim 1, wherein the pharmaceutically acceptable salt is a base addition salt comprising a metal counterion selected from the group consisting of sodium, potassium, calcium, magnesium, lithium, ammonium, manganese, zinc, iron, and copper.

11. The method of claim 10, wherein the pharmaceutically acceptable salt is sodium.

12. The method of claim 1, wherein said diabetes is Type II diabetes.

13. The method of claim 1, wherein said diabetes is Type I diabetes.

14. The method of claim 1, wherein administration of said compound results in one or more of the following biological activities in the subject:
an increase in insulin secretion;
an increase in insulin sensitivity;
a decrease in insulin resistance;
a decrease in blood glucose level; and
a decrease of blood triglyceride level.

15. The method of claim 14, wherein administration of said compound reduces blood glucose level.

16. The method of claim 14, wherein administration of said compound maintains or increases insulin level in a subject requiring protection and/or regeneration of pancreatic islets.

17. A method for modulating glucose, insulin and/or triglyceride levels in a subject in need thereof, comprising the step of administering to said subject a compound represented by Formula I, as defined in claim 1, or a pharmaceutically acceptable salt thereof, at a dose of 0.1 to 5 mg/kg per day.

18. The method of claim 17, wherein the dose is 0.1 to 1.0 mg/kg per day.

19. A method for increasing insulin secretion and/or increasing insulin sensitivity and/or decreasing insulin resistance in a subject in need thereof, comprising the step of administering to said subject a compound represented by Formula I, as defined in claim 1, or a pharmaceutically acceptable salt thereof, at a dose of 0.1 to 5 mg/kg per day.

20. The method of claim 19, wherein the dose is 0.1 to 1.0 mg/kg per day.

21. The method of claim 1, wherein the subject is afflicted by hyperglycemia, glucose intolerance, insulin resistance, hyperinsulinemia, dyslipidemia and/or loss of pancreatic function.

22. The method of claim 1, wherein the compound is administered concomitantly with a second therapeutic agent.

23. The method of claim 22, wherein the second therapeutic agent is a compound for lowering or modulating blood glucose level.

24. The method of claim 22, wherein the second therapeutic agent is metformin or is a thiazolidinedione.

25. A method for reducing blood triglyceride in a subject in need thereof, comprising administering to said subject a compound represented by Formula I, as defined in claim 1, or a pharmaceutically acceptable salt thereof, at a dose of 0.1 to 5 mg/kg per day, wherein said compound reduces blood triglyceride level.

26. The method of claim 25, wherein the dose is 0.1 to 1.0 mg/kg per day.

27. The method of claim 25, wherein the subject is afflicted by diabetic dyslipidemia and/or metabolic syndrome.

28. The method of claim 1, wherein the compound is administered orally.

29. The method of claim 1, wherein said compound is represented by one of the following structures:

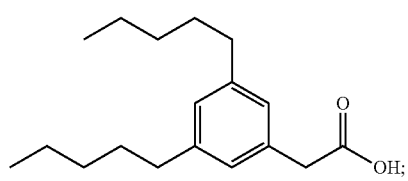

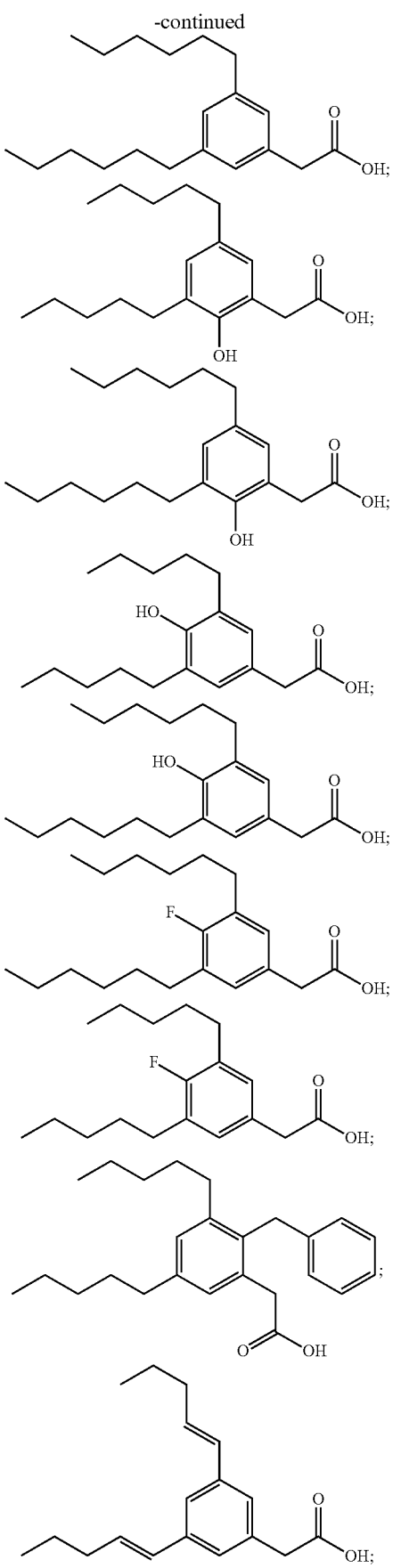

-continued
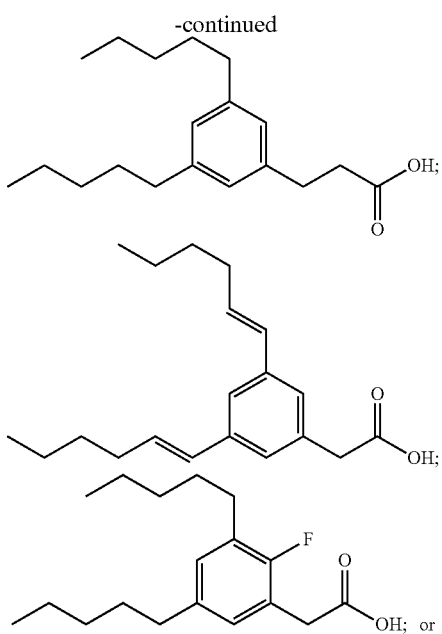
-continued
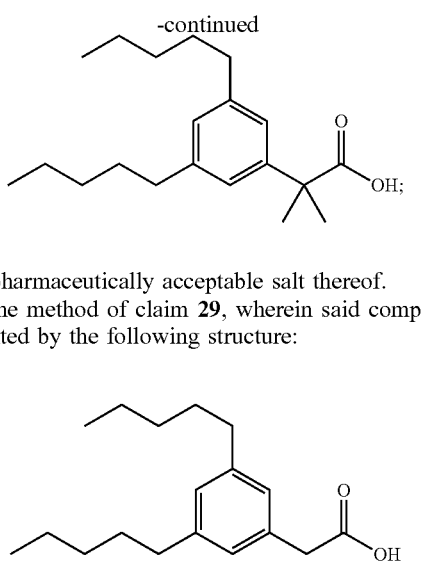
or a pharmaceutically acceptable salt thereof.
30. The method of claim 29, wherein said compound is represented by the following structure:
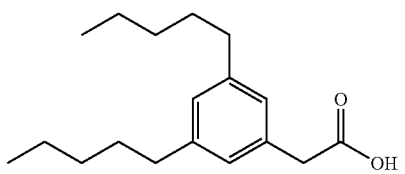 [SMILES: CCCCCc1cc(CCCCC)cc(CC(=O)O)c1]
or pharmaceutically acceptable salt thereof.
* * * * *

UNITED STATES PATENT AND TRADEMARK OFFICE
CERTIFICATE OF CORRECTION

PATENT NO. : 10,105,331 B2
APPLICATION NO. : 15/515048
DATED : October 23, 2018
INVENTOR(S) : Lyne Gagnon and Brigitte Grouix It is certified that error appears in the above-identified patent and that said Letters Patent is hereby corrected as shown below:

In the Specification

Column 5:
Line 29, "or is preferably C5 alkyl," should read -- or is preferably C6 alkyl, --.

Column 19:
Line 10, "133 adrenergic receptor" should read -- β3 adrenergic receptor --.

Column 34:
Line 32, "cooled to 000° C" should read -- cooled to 0° C --.

Signed and Sealed this
Second Day of July, 2019

Andrei Iancu
*Director of the United States Patent and Trademark Office*